(12) United States Patent
Iqbal et al.

(10) Patent No.: US 11,207,674 B2
(45) Date of Patent: *Dec. 28, 2021

(54) METHOD OF CUSTOMIZING A UNIVERSAL REAGENT CARTRIDGE WITH A LYOPHILIZED TARGET-SPECIFIC REAGENT

(71) Applicants: Shazi Iqbal, Danville, CA (US); Michael C L Vickery, Birmingham, AL (US)

(72) Inventors: Shazi Iqbal, Danville, CA (US); Michael C L Vickery, Birmingham, AL (US)

(73) Assignee: BIOGX, INC., Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,196

(22) Filed: Aug. 9, 2018

(65) Prior Publication Data

US 2019/0134624 A1    May 9, 2019

Related U.S. Application Data

(60) Provisional application No. 62/543,352, filed on Aug. 9, 2017.

(51) Int. Cl.
*B01L 3/00* (2006.01)
*C12Q 1/6806* (2018.01)
(Continued)

(52) U.S. Cl.
CPC .............. *B01L 3/502* (2013.01); *B01L 3/545* (2013.01); *C12Q 1/6806* (2013.01);
(Continued)

(58) Field of Classification Search
CPC ....... B01L 3/502; B01L 3/545; C12Q 1/6806; G06K 19/06028
See application file for complete search history.

(56) References Cited

U.S. PATENT DOCUMENTS

| 3,888,113 A | 6/1975 | Miranda |
| 5,440,725 A | 8/1995 | Weller et al. |

(Continued)

FOREIGN PATENT DOCUMENTS

| WO | 2005087951 A2 | 9/2005 |
| WO | 2017093763 A2 | 6/2017 |

(Continued)

OTHER PUBLICATIONS

International Search Report (ISR) for International Publication No. WO2020033778, International patent application No. PCT/US20191/045818, International filing date: Aug. 8, 2019; Title: "Method of Customizing a Universal Reagent Cartridge with a Lyophilized Target-Specific Reagent", Inventors; Iqbal, Vickery; Applicant BIOGX, INC., pp. 1-4.

(Continued)

*Primary Examiner* — Angela M. Bertagna
*Assistant Examiner* — Carolyn L Greene
(74) *Attorney, Agent, or Firm* — Mark P Kahler

(57) ABSTRACT

Customization of a universal reagent cartridge with a lyophilized target-specific PCR component reagent is disclosed. The universal reagent cartridge includes multiple chambers populated with predetermined non-target-specific reagents therein. A custom reagent storage device that stores a lyophilized, target-specific reagent is provided and is configured to be end user insertable into the universal reagent cartridge to customize the universal reagent cartridge with the target-specific reagent.

8 Claims, 24 Drawing Sheets

(51) Int. Cl.
*G06K 19/06* (2006.01)
*B01L 3/02* (2006.01)

(52) U.S. Cl.
CPC ...... *G06K 19/06028* (2013.01); *B01L 3/0275* (2013.01); *B01L 3/50825* (2013.01); *B01L 3/52* (2013.01); *B01L 2200/02* (2013.01); *B01L 2200/0647* (2013.01); *B01L 2200/14* (2013.01); *B01L 2200/16* (2013.01); *B01L 2300/021* (2013.01); *B01L 2300/087* (2013.01); *B01L 2300/0832* (2013.01)

(56) References Cited

U.S. PATENT DOCUMENTS

| | | | |
|---|---|---|---|
| 5,556,598 | A | 9/1996 | Raybuck |
| 8,048,386 | B2 | 11/2011 | Dority |
| 8,216,530 | B2 | 7/2012 | Handique |
| 8,343,426 | B2 | 1/2013 | Song |
| 9,156,032 | B2 | 10/2015 | Peterson |
| 9,248,422 | B2 * | 2/2016 | Ching ............... B01F 11/0071 |
| 9,394,086 | B2 | 7/2016 | Jordan |
| 9,519,000 | B2 | 12/2016 | Wilson |
| 9,689,029 | B2 | 6/2017 | Thorne |
| 2006/0068399 | A1 | 3/2006 | McMillan |
| 2008/0014114 | A1 | 1/2008 | Van Atta |
| 2008/0193946 | A1 | 8/2008 | McMillan |
| 2008/0193995 | A1 | 8/2008 | Tajima |
| 2012/0100546 | A1 | 4/2012 | Lowery |
| 2014/0098252 | A1 | 10/2014 | Chang |
| 2016/0101421 | A1 | 4/2016 | Ching |
| 2017/0021356 | A1 | 1/2017 | Dority |
| 2017/0137871 | A1 | 5/2017 | Lai |
| 2018/0214864 | A1 | 8/2018 | Lai |

FOREIGN PATENT DOCUMENTS

| | | |
|---|---|---|
| WO | 2020033778 A1 | 2/2020 |
| WO | 2020033781 A1 | 2/2020 |

OTHER PUBLICATIONS

Written Opinion of the Searching Authority (WOSA) for International Publication No. No. WO2020033778, International Patent application No. PCT/US2019/045818, International filing date: Aug. 8, 2019; Title: "Method of Customizing a Universal Reagent Cartridge with a Lyophilized Target-Specifc Reagent", Inventors: Iqbal, Vickery; Applicant: BIOGX, NC., pp. 1-5.

International Search Report (ISR) for International Publication No. WO2020033781, International patent application PCT/US2019/045821, International filing date: Aug. 9, 2019; Title: "Reagent Storage Device for Storing a Target-Specific Reagent", Inventors: Iqbal, Vickery; Applicant: BIOGX, INC., pp. 1-3.

Written Opinion of the Searching Authority (WOSA) for International Publication No. WO2020033781, International Patent application No. PCT/US2019/045821, International filing date: Aug. 9, 2019; Title: "Reagent Storage Device for Storing a Target-Specific Reagent", Inventors: Iqbal, Vickery; Applicant: BIOGX, INC., pp. 1-5.

CDRH—"Guidance for Industry and FDA Staff; Commercially Distributed Analyte Specific Reagents (ASRs): Frequently Asked Questions", Sep. 7, 2016, pp. 1-13.

Cepheid—"The New GeneXpert System", Ceipheid Brochure, 2012, pp. 1-12.

New England BioLabs—"DNA Amplification, PCR & qPCR", (downloaded from neb.com on Jul. 8, 2017), pp. 1-3.

Frey—"Frey Scientific Micropipette Tips", (downloaded from schoolspecialty.com on Nov. 27, 2018), p. 1.

Shifreen—"Navigating the Analyte Specific Reagents Regulations", 2003, pp. 1-42.

Klingenberg—"The Original Micropipette", The Scientist, Jan. 2006, pp. 1-5.

Miller—"The Indispensable Dispenser: The Micropipetter", The Scientist, Nov. 1997, pp. 1-15.

Thermo—"Automation Tips and Accessories", Thermo Scientific, 2013, pp. 1-32.

\* cited by examiner

ADD CUSTOMER
SPECIFIED REAGENTS

ADD CUSTOMER
SPECIFIED REAGENTS

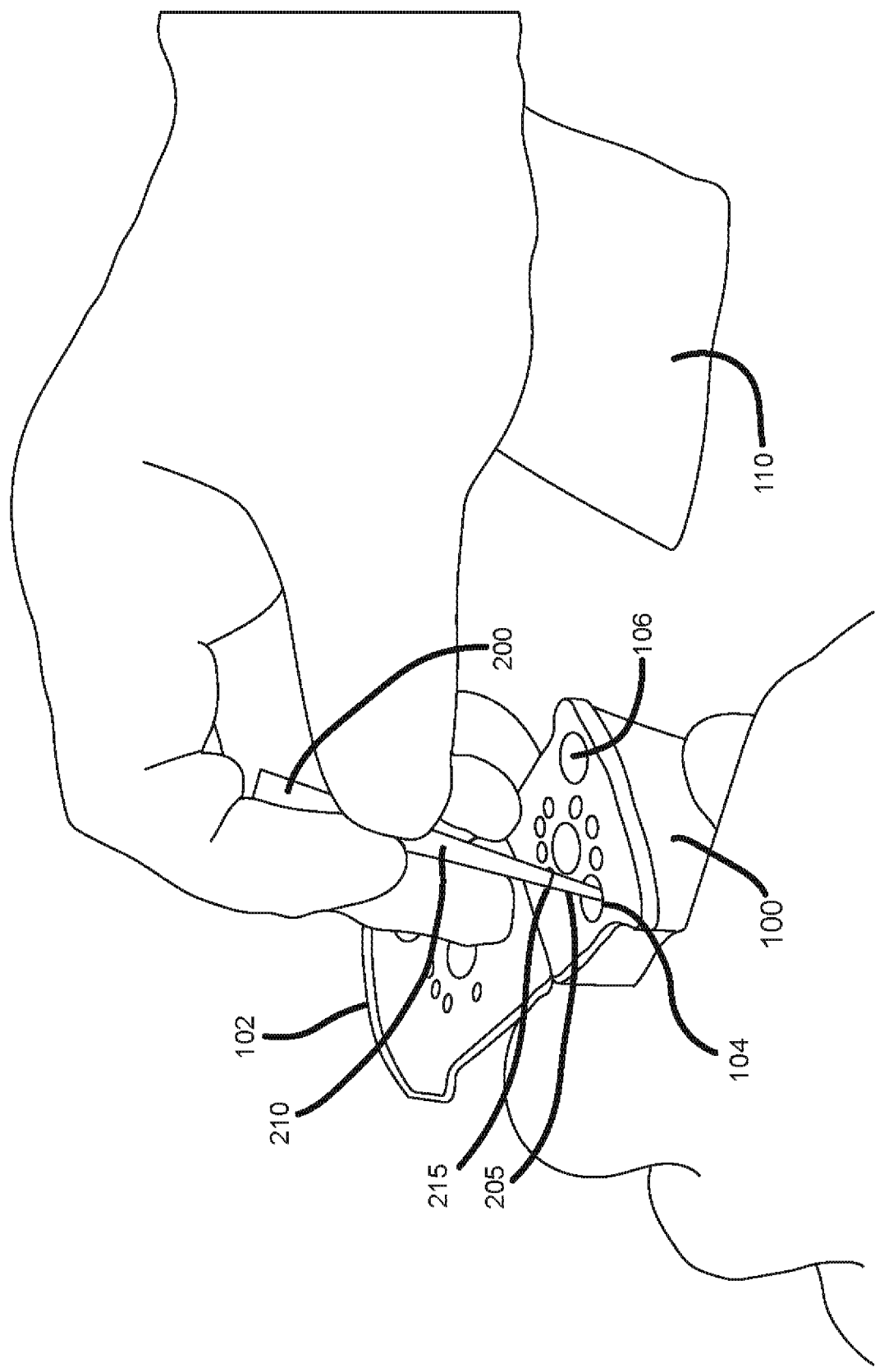

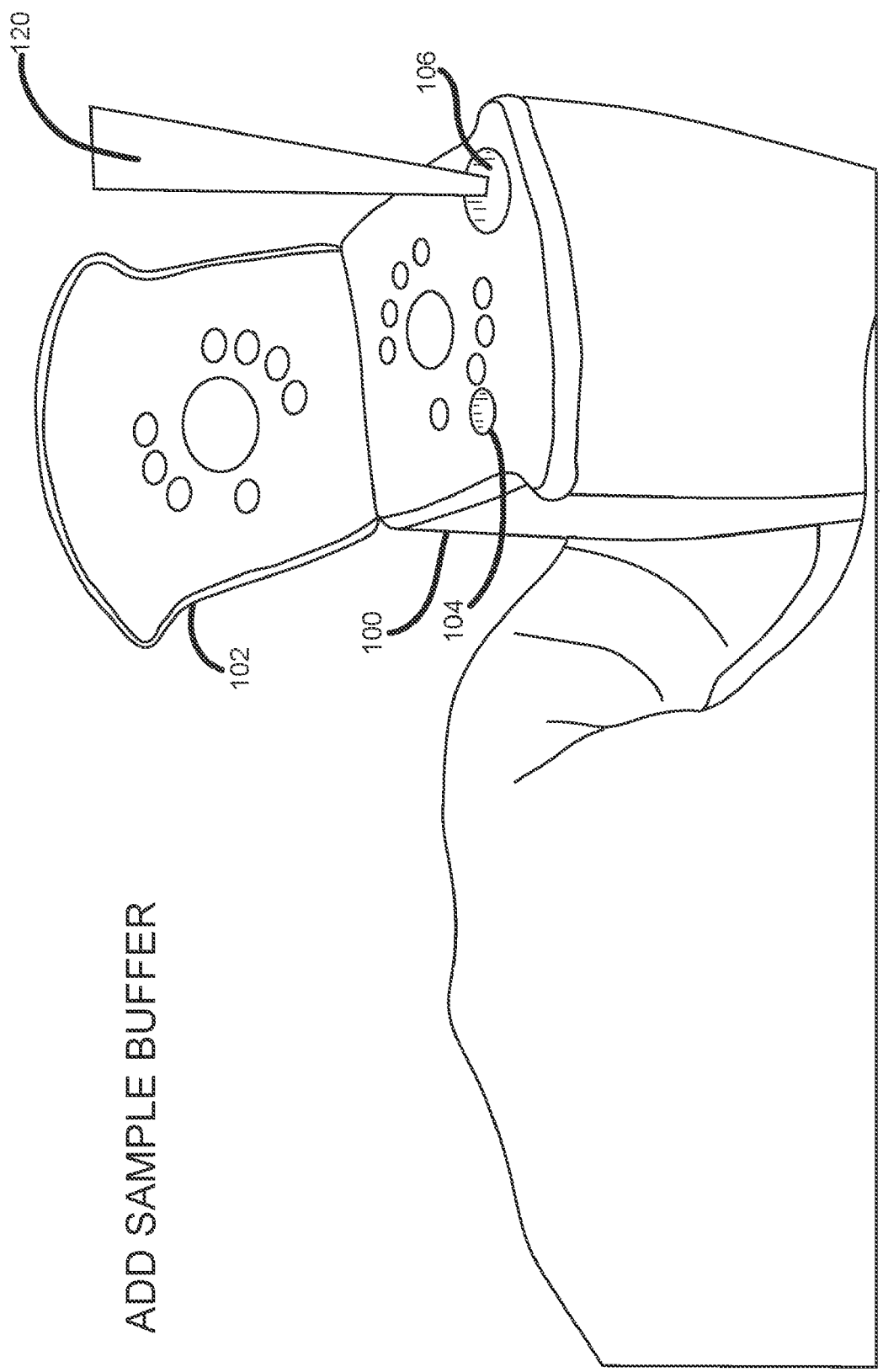

ADD SAMPLE BUFFER

ADD SAMPLE BUFFER

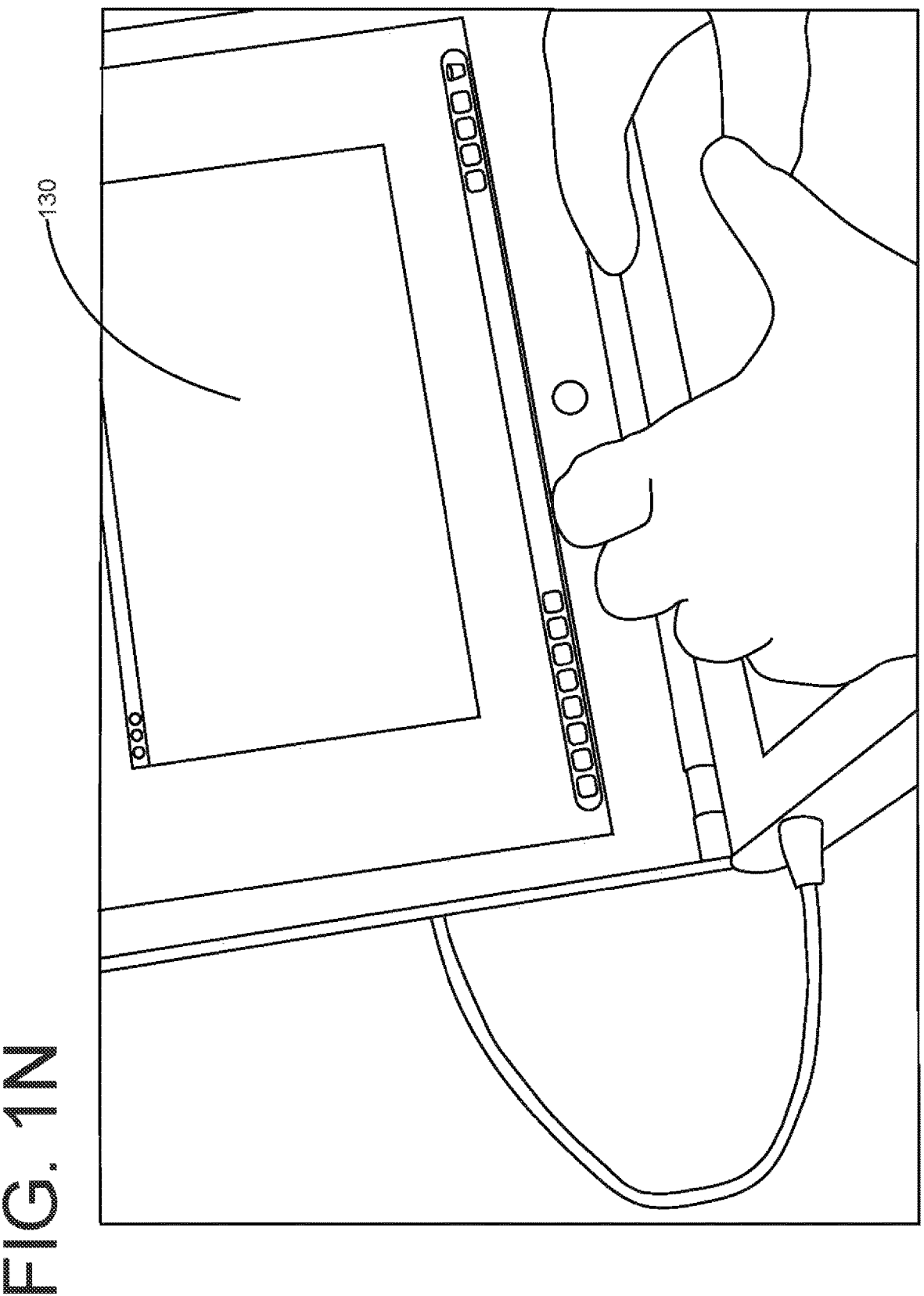

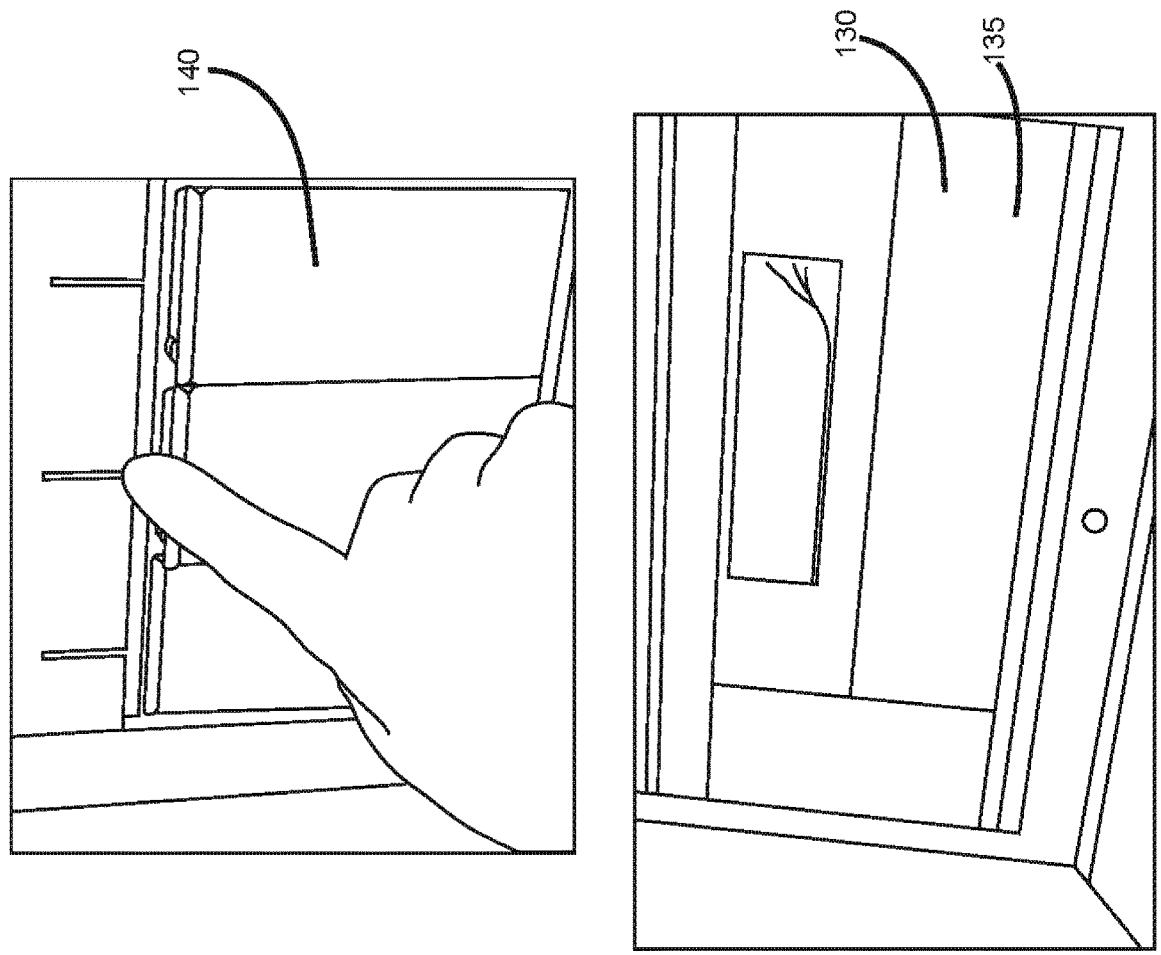

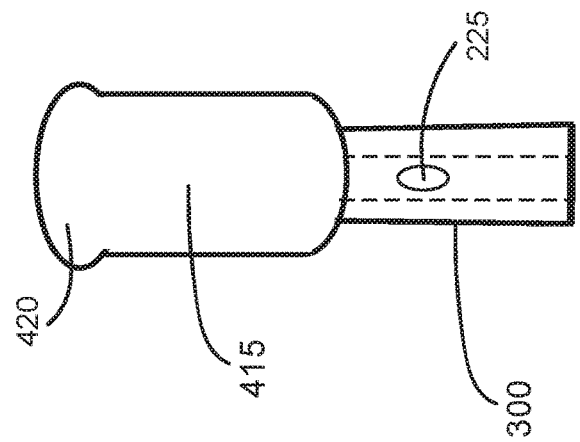
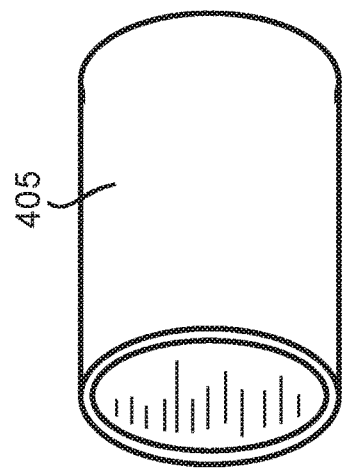
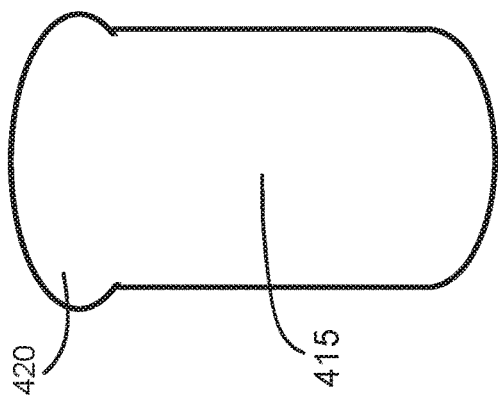

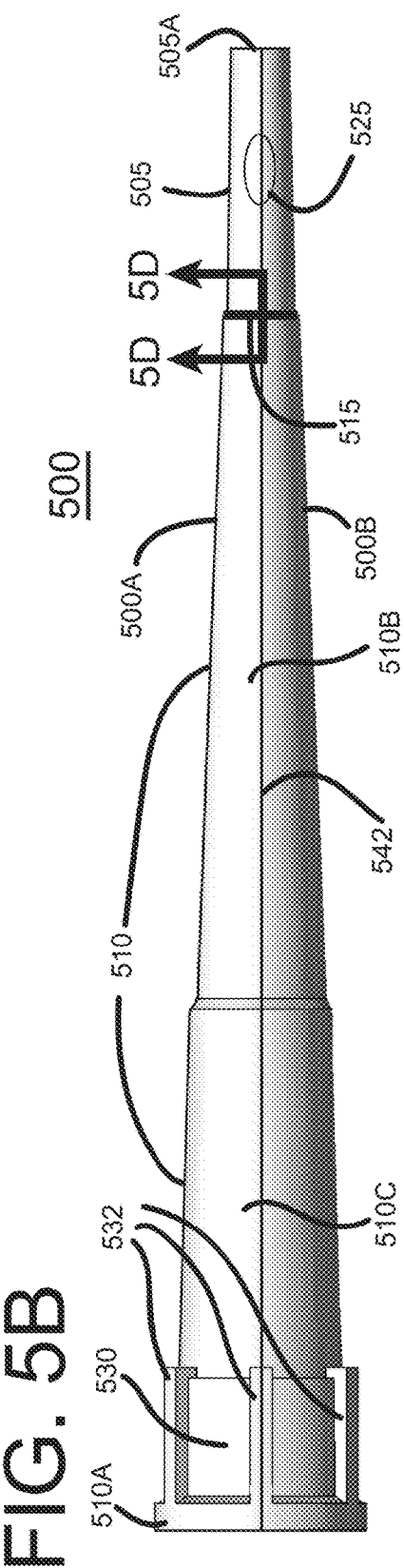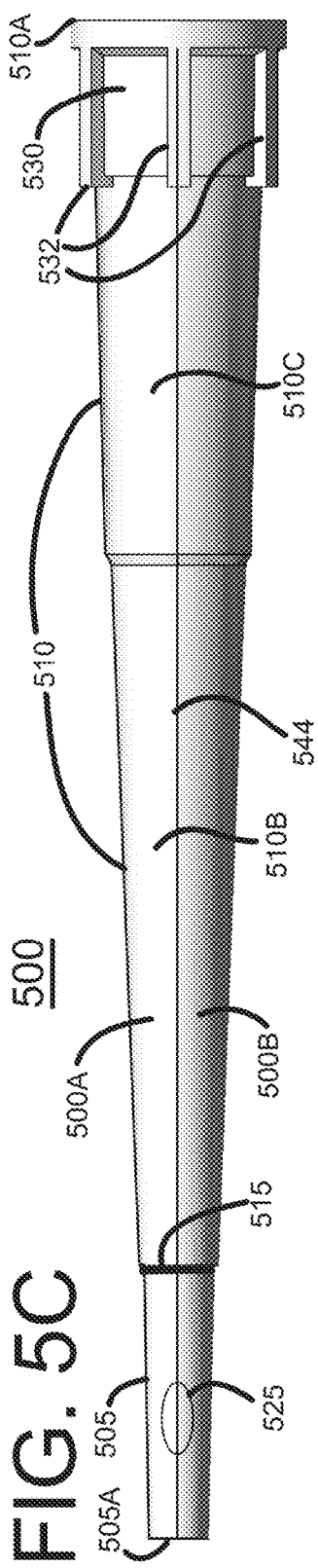

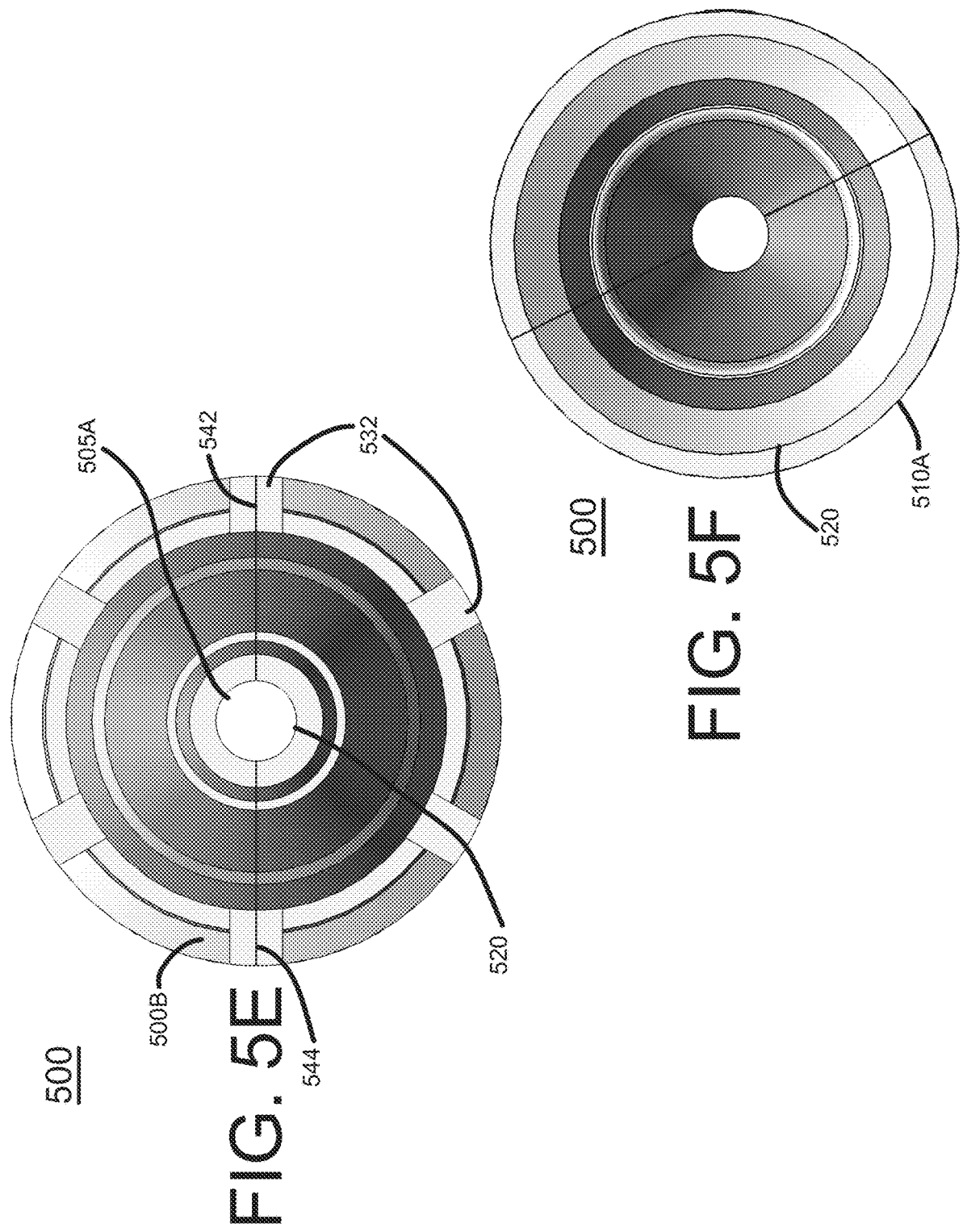

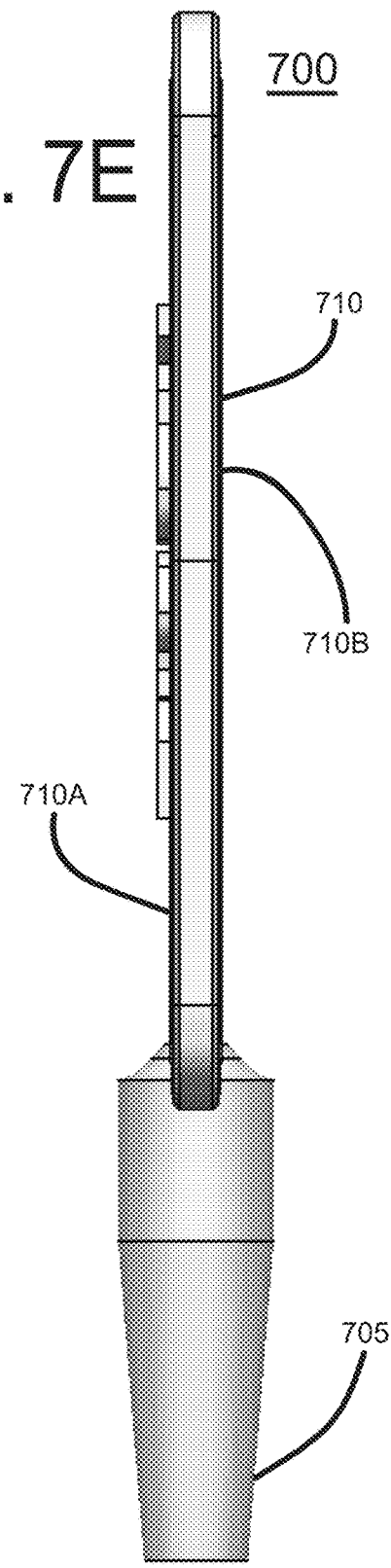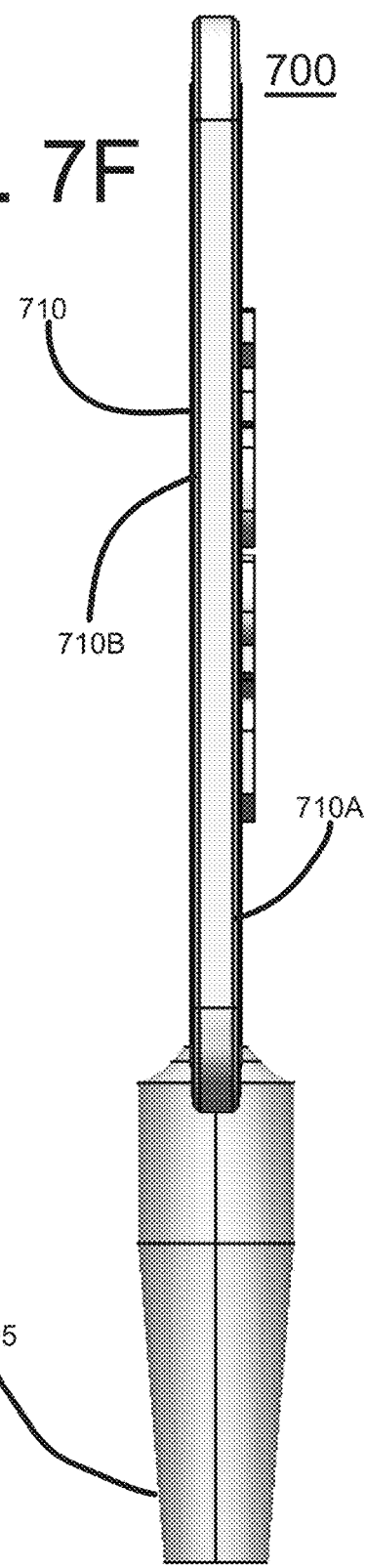

METHOD OF CUSTOMIZING A UNIVERSAL REAGENT CARTRIDGE WITH A LYOPHILIZED TARGET-SPECIFIC REAGENT

CROSS REFERENCE TO RELATED PATENT APPLICATIONS

This patent application claims priority to Provisional U.S. Patent Application Ser. No. 62/543,352, filed Sep. 9, 2017, by inventors Shazi S. Iqbal and Michael C. L. Vickery, the disclosure of which is incorporated herein by reference in its entirety.

BACKGROUND

The disclosures herein relate generally to molecular testing, and more specifically to the molecular testing of samples for diagnostic purposes. The disclosures herein also relate to fluidic analysis systems that receive cartridges containing reagents used for sample testing by such fluidic analysis systems.

BRIEF SUMMARY

In one embodiment, a method is disclosed for customizing a universal reagent cartridge with a lyophilized target-specific reagent, wherein the method includes providing a universal reagent cartridge including a plurality of chambers populated with predetermined non-target-specific reagents therein. The method further includes providing a custom reagent storage device that stores a lyophilized, target-specific reagent therein, the custom reagent storage device being configured to be end user insertable into the universal reagent cartridge to customize the universal reagent cartridge with the target-specific reagent. In accordance with the disclosed method, the target-specific reagent may be a lyophilized, target-specific polymerase chain reaction (PCR) component. In accordance with one embodiment of the method, the target-specific reagent is designated for a predetermined target DNA or RNA gene sequence in a sample. The method may further include inserting a portion of the custom reagent storage device into the universal reagent cartridge to customize the universal reagent cartridge with the target-specific reagent.

In another embodiment, a reagent storage device is disclosed that includes a tubular member including opposed first and second open ends. A break-off region is situated a predetermined distance from the first open end, the break-off region dividing the tubular member into a reagent storage section between the first open end and the break-off region, and a remaining_section between the break-off region and the second open end. The reagent storage section is configured to store a lyophilized, target-specific reagent therein. The break-off region exhibits a lower structural integrity than the remainder of the reagent storage device such that the reagent storage section breaks-off from the remaining section when the reagent storage section is pressed against a port in a reagent cartridge that includes a plurality of predetermined reagents. In this manner the lyophilized, target-specific reagent enters the reagent cartridge via the port to customize the reagent cartridge with the target-specific reagent.

BRIEF DESCRIPTION OF THE DRAWINGS

The appended drawings illustrate only exemplary embodiments of the invention and therefore do not limit its scope because the inventive concepts lend themselves to other equally effective embodiments.

FIG. 1G is a representation of the reagent storage section of the target specific PCR component storage device being placed in a dedicated port of the universal cartridge.

FIG. 1K depicts a sample buffer being added to the sample port of the universal cartridge.

FIG. 1N is a representation of a general purpose computer executing a test application to receive test information input.

FIG. 1Q depicts a user closing the test bay of the test instrument so that testing can commence.

FIG. 1R is a representation of the general purpose computer of FIG. 1N showing test results after executing the test application.

FIG. 4A depicts a cap that is mountable on the target specific PCR component storage device to facilitate handling of the storage device without contamination.

FIG. 4B depicts another embodiment of the cap that includes a bulbous ejector at one end.

FIG. 4C depicts the cap of FIG. 4B mounted on one end of the target specific PCR component storage device.

FIG. 5B is a side elevational view of the target specific PCR component storage device.

FIG. 5C is another side elevational view of the target specific PCR component storage device.

FIG. 5D is a cross section of the side elevational view of the target specific PCR component storage device of FIG. 5B taken along section line 5D-5D.

FIG. 5D' is a cross section of the side elevational view of the target specific PCR component storage device of FIG. 5B taken along section line 5D-5D but showing an alternative embodiment.

FIG. 5E is an end view of the target specific PCR component storage device as viewed from the narrow end thereof.

FIG. 5F is an end view of the target specific PCR component storage device as viewed from the wide end thereof.

FIG. 7E is a right side elevation view of the tab of FIG. 7A.

FIG. 7F is a left side elevation view of the tab of FIG. 7A

DETAILED DESCRIPTION

Figure 1A:
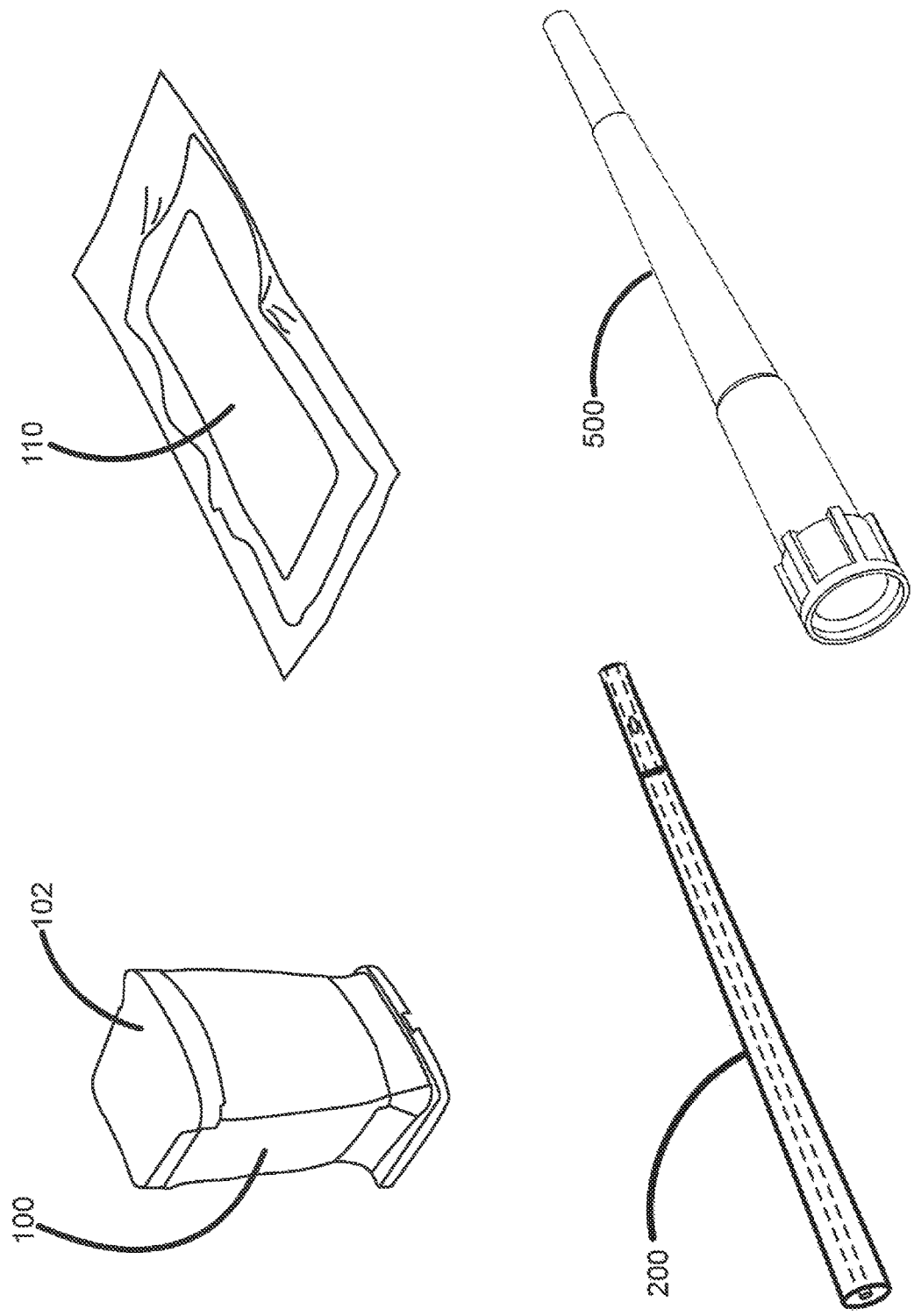
FIG. 1A is a representation of a universal cartridge shown together with different embodiments of a target specific PCR component storage device including a break-off region.

In one embodiment, a reagent storage device and testing methodology are disclosed that may be used with a molecular diagnostic assay instrument to customize the testing of samples by the instrument.

Molecular diagnostic assay testing instruments may include one or more testing bays that receive respective assay cartridges which contain predetermined reagents and samples for testing purposes. A particular cartridge may include multiple chambers with different reagents, as well as a chamber in which the sample to be tested is inserted. After the user places a cartridge with its reagents and sample in a testing bay of the instrument, the instrument processes the sample by using the supplied reagents. For example, this processing may include DNA and RNA extraction and purification. The instrument may also perform polymerase chain reaction (PCR) amplification on the sample to amplify a targeted DNA or RNA gene sequence. In this manner, the target may be amplified millions-fold or billions-fold and further be provided with a fluorescent tag. For example, if the test is to detect a particular pathogen or disease cancer gene, the test targets DNA that is specific to that disease. The target DNA is amplified billions-fold. The instrument then fluorometrically detects the amplified target using optical readers to detect the targeted disease, if present. The testing instrument includes the mechanical, electromechanical, optical, electronic and other structures needed to process the cartridge. Notably, the testing instrument includes optical detection apparatus to detect the presence of a targeted gene sequence.

Testing instrument manufacturers typically manufacture the multi-chamber cartridge and preload the chambers of the cartridge with all of the reagents required for a particular target detection protocol. In other words, the cartridge is prepackaged with all of the necessary reagents installed in the cartridge before the cartridge is shipped to the customer. The cartridge manufacturer ships the preloaded cartridge to a customer, and the customer receives the preloaded cartridge in ready-to-use condition to detect a particular target. The customer adds a sample to the cartridge wherein the sample will be tested for presence of the particular target that the manufacturer effectively "programmed" into the cartridge. The sample may be a blood sample, saliva sample, sputum sample, i.e. any sample for which detection of the specific target sequence is desired. As used herein, the term "customer" may include an "end-user", or more simply, the "user", i.e. the person actually performing the test.

In the above described testing system, each cartridge is dedicated to a specific target for detection. First, the customer places an order with the manufacturer. The customer order specifies a particular target sequence to be detected. In response, the manufacturer prepares a unique cartridge that is populated with particular reagents for detecting a specific target. This approach may result in high manufacturing costs because, with each cartridge effectively being unique, economy of scale is not possible. In this approach, quality control costs may also be very high. Moreover, the customer or user is foreclosed from detecting some target other than the particular target for which the cartridge was built and dedicated by the manufacturer.

In accordance with the advanced testing apparatus and methodology disclosed herein, a "cartridge provider" (for example a manufacturer), preloads generic reagents in the chambers of a cartridge. This cartridge will be referred to as a "universal cartridge". The universal cartridge includes the generic reagents needed for testing a sample, but does not initially store a target specific reagent, also referred to as a target specific PCR component. The universal cartridge includes a port that is dedicated to receiving the target specific PCR component after the customer receives the universal cartridge containing the generic reagents from the manufacturer.

As an example, a customer desires to test for a particular target sequence. The customer orders and receives a universal cartridge from the "cartridge provider", for example the manufacturer. As described above, the universal cartridge stores the generic reagents for the general type of test that the customer desires to conduct. In this particular example, the customer desires to test for a first target sequence by using a first target specific PCR component and also desires to test for a second target sequence by using a second target specific PCR component. The customer places an order with a "target provider" to provide a first target specific PCR component and a second target specific PCR component. The "target provider" stores the ordered first target specific PCR component in a first reagent storage device. The "target provider" stores the ordered second target specific PCR component in a second regent storage device. The "reagent storage device" may be configured as a plastic tube that stores the target specific PCR component, as described below in more detail with respect to the disclosed reagent storage tip.

The customer receives the first and second reagent storage devices from the target provider. The customer also orders and receives multiple universal cartridges from the cartridge provider. The customer is now fully equipped with the ability to customize a universal cartridge to detect a particular target. In a first example, the user may wish to customize the first universal cartridge with a first target specific PCR component to detect a particular target sequence. To do so, the customer takes the first reagent storage device and transfers the contents of the first reagent storage device to a dedicated port of the first universal cartridge. This port is dedicated to receiving the target specific PCR component. The first universal cartridge is now ready for testing by the testing instrument because the first universal cartridge is now populated with both the generic reagents needed for the test as well as the target specific PCR component needed to target and test the desired target sequence. The customer adds the sample to be tested into the first universal cartridge, and then moves the first universal cartridge to an open testing bay of the molecular testing instrument. The testing instrument performs the test and provides output to the user to indicate the presence or absence of the target sequence.

In a second example, the user may wish to customize the second universal cartridge with a second target specific PCR component to test for a different target sequence than the particular target sequence associated with the first target specific PCR component of the first test. To do so, the customer takes the second reagent storage device and transfers the contents of the second reagent storage device to the dedicated port of the universal cartridge. The second universal cartridge is now ready to conduct a test because it is now populated with both the generic reagents needed for the test as well as the second target specific PCR component needed to test for the new target sequence. As before, the user/customer adds the sample to be tested into the second universal cartridge, and then moves the second universal cartridge to an open testing bay of the molecular testing instrument. As before, the testing instrument performs the test and provides output to indicate the presence or absence of the target sequence. Those skilled in the art will appreciate that while the 2 examples above are serial tests, these tests may be conducted in parallel to save time.

Referring now to FIG. 1A, the customer receives a universal cartridge 100 from the cartridge provider and a target specific PCR component from the target provider. Cartridges that are useful as a universal cartridge when modified as described below are seen in U.S. Pat. Nos. 8,048,386 and 9,394,086, the disclosures of which are incorporated herein by reference in their entirety. In FIG. 1A, the target specific PCR component is stored in a reagent storage device 200 or a reagent storage device 500. For example, reagent storage device 200, with the target specific PCR component therein, is packaged in a sealed foil wrapper 110 for protection. The cap 102 of the universal cartridge 100 is shown as being closed.

The universal cartridge 100, as received from the "cartridge provider", already contains the generic reagents for a particular test type that the customer desires to run on the sample. The customer may now customize the test to detect a particular target sequence by adding the customer specified target reagent from reagent storage device 200 or 500 (after removal from the sealed foil wrapper 102) to the universal cartridge 100, as discussed in more detail below. A "target provider" supplies the reagent storage device 200 or 500 containing the desired target specific PCR component according to the target sequence order that the customer sends to the "target provider".

Figure 1B:
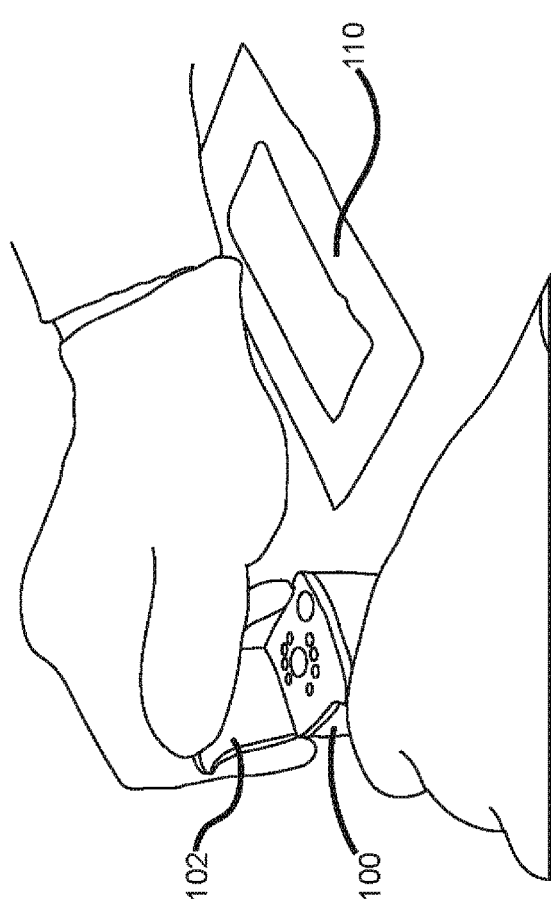
FIG. 1B is a representation of the universal cartridge being opened by a user and is shown together with a foil wrapper that contains a target specific PCR component storage device therein.
Figure 1C:
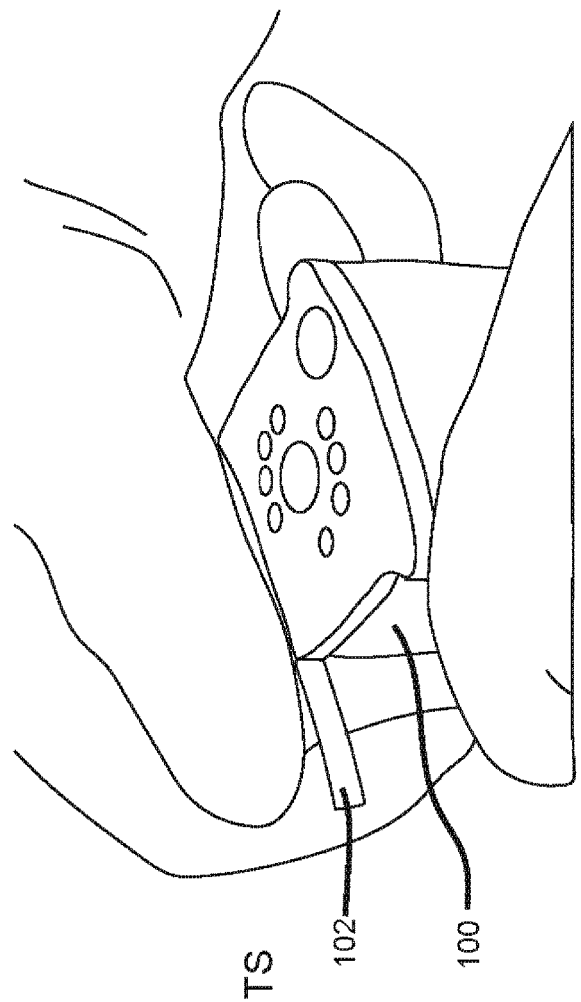
FIG. 1C is a representation the universal cartridge being further opened by a user.
Figure 1D:
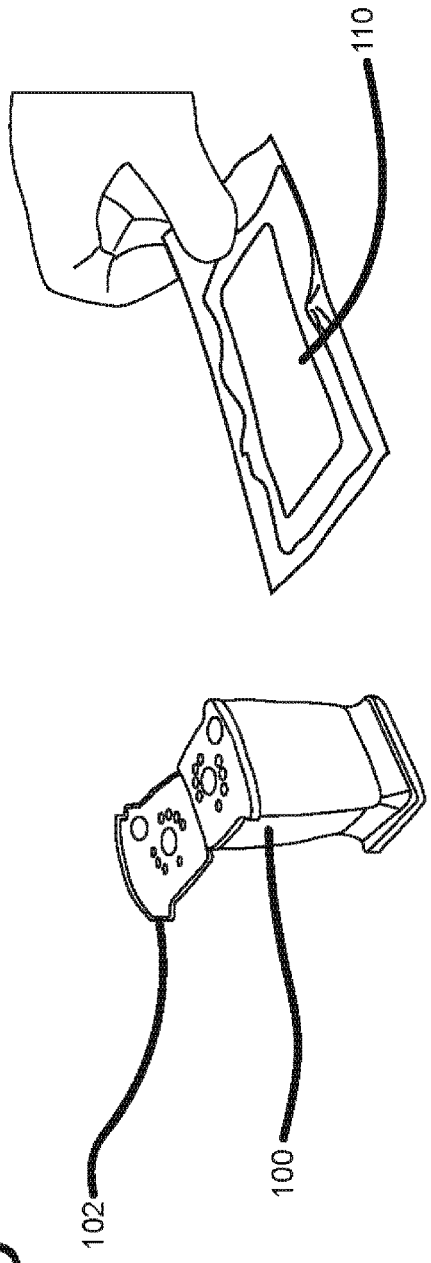
FIG. 1D is a representation of the opened universal cartridge adjacent the unopened foil wrapper.
Figure 1E:
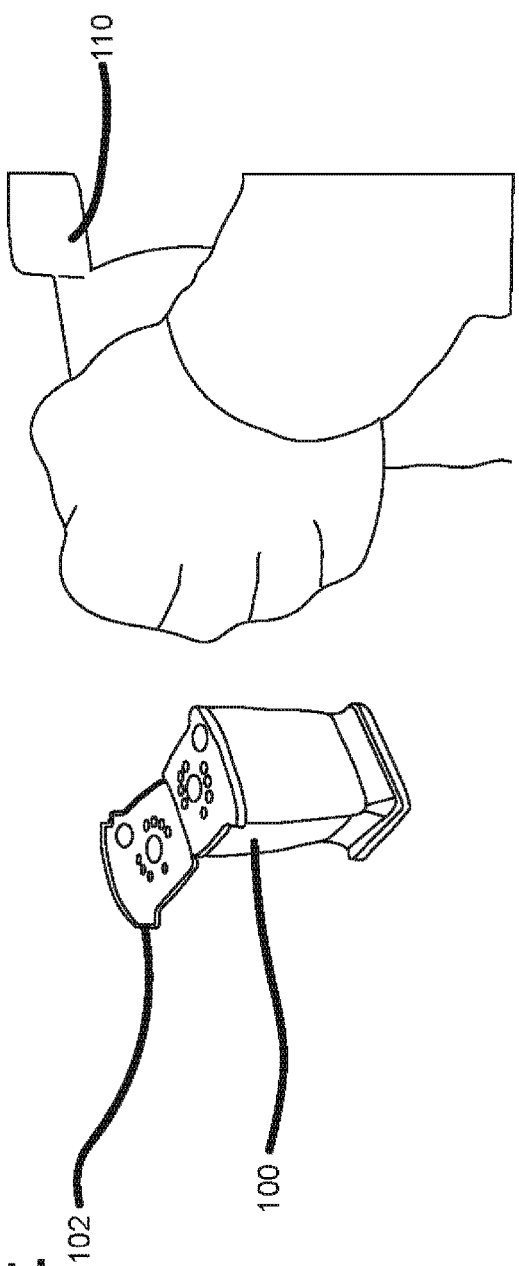
FIG. 1E depicts the opening of the foil wrapper containing the target specific PCR component storage device.

The customer, i.e. user, opens the cap 102 of universal cartridge 100 as seen in FIG. 1B and FIG. 1C. Next, the customer opens foil wrapper 110 to access the reagent storage device 200 or 500 with the selected target specific PCR component therein, as seen in FIG. 1D and FIG. 1E.

Figure 1F:
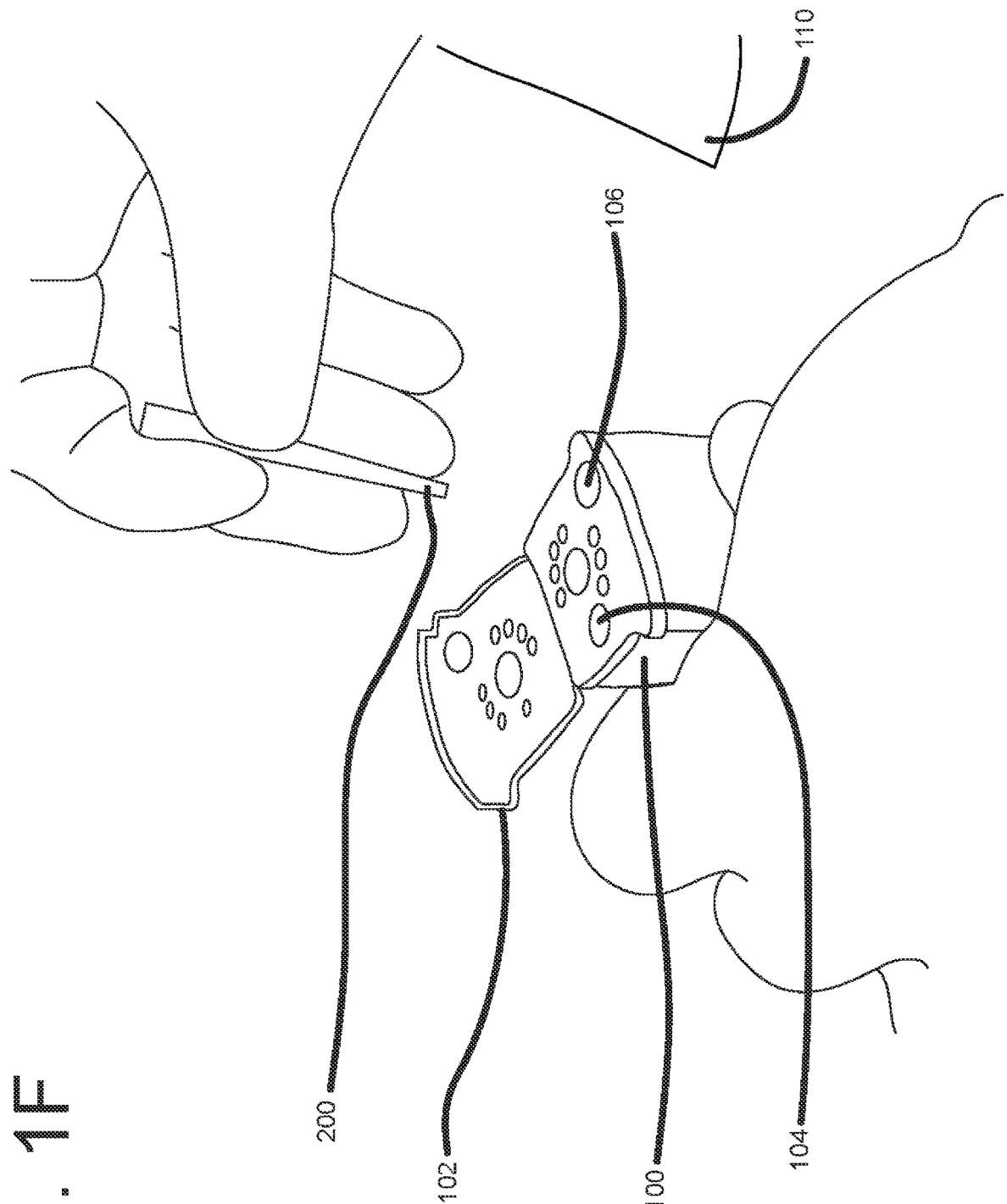
FIG. 1F is a representation of a user moving the target specific PCR component storage device toward the universal cartridge.

As seen more clearly in FIG. 1F, universal cartridge 100 includes a dedicated port 104 for receiving the target specific PCR component. Universal cartridge 100 also includes a sample port 106 that receives a sample under test after the target specific PCR component is deposited in dedicated port 104. Before depositing the sample in sample port 106, the customer moves reagent storage device 300 toward the dedicated target specific PCR component port 104 of universal cartridge 100 as shown in FIG. 1F. In one embodiment, the reagent storage device may take the form of a plastic tube, such as reagent storage device 200 of FIG. 2A or reagent storage device 500 of FIG. 5A. The reagent storage device may be tubular and/or generally conical in shape. The reagent storage device tube may be fabricated of plastic material. In one embodiment, a reagent storage device 200 may be divided into two sections, namely a reagent storage section 205 and a remaining section 210, as seen and discussed in more detail with reference to FIGS. 2A-2B below. However, briefly, the reagent storage section 205 is divided from the remaining section 210 by a score line 215. The score line 215 is sufficiently deep to allow the reagent storage section 205 to break-off, i.e. snap off, and separate from, the remaining section 210 at the score line 215, when the user applies torque to reagent storage section 120 against the side of dedicated port 104. The reagent storage section contains the target specific PCR component in a lyophilized form.

Figure 1H:
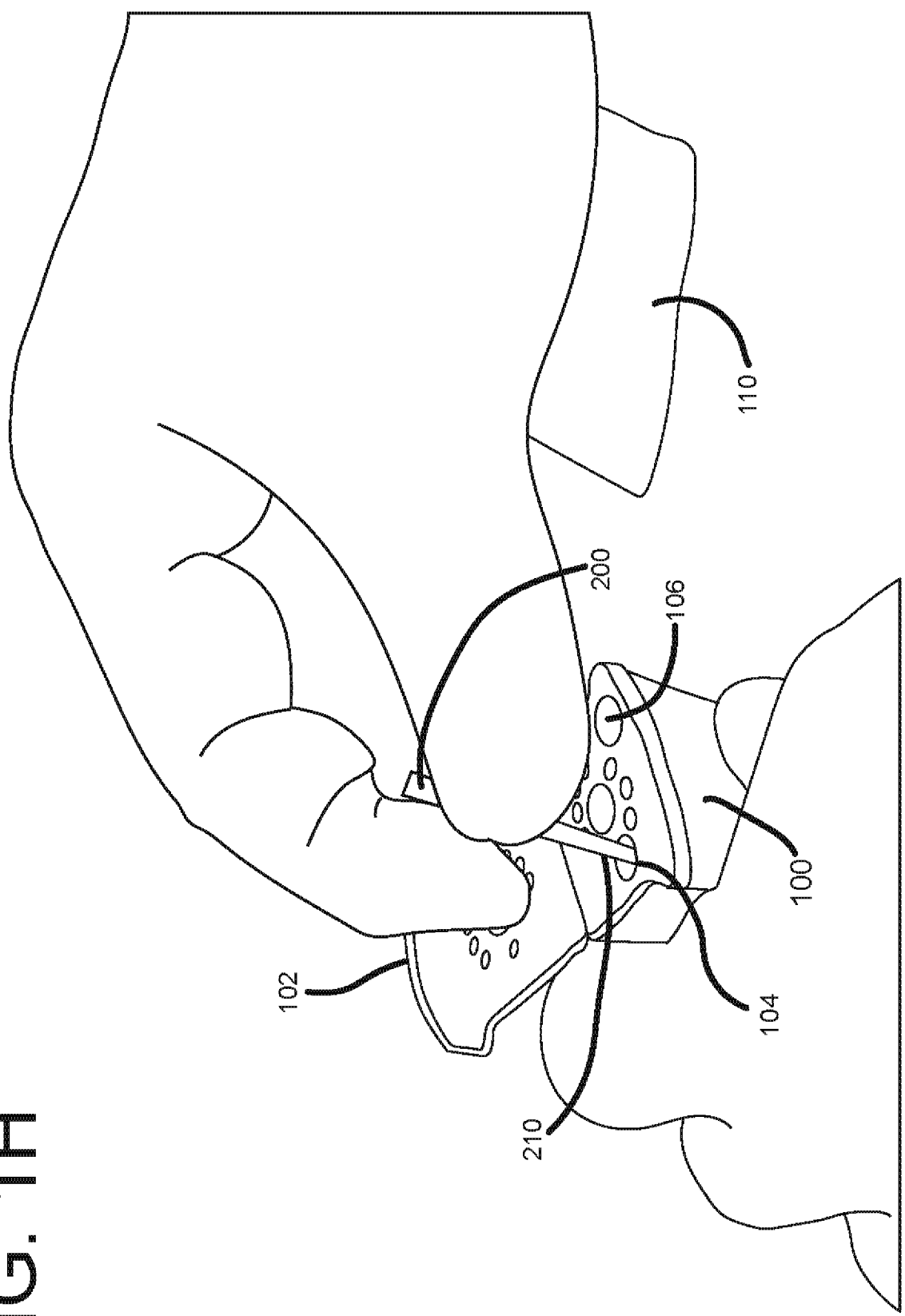
FIG. 1H is a representation of the reagent storage section of the target specific PCR component storage device being placed further into the dedicated port of the universal cartridge.
Figure 1I:
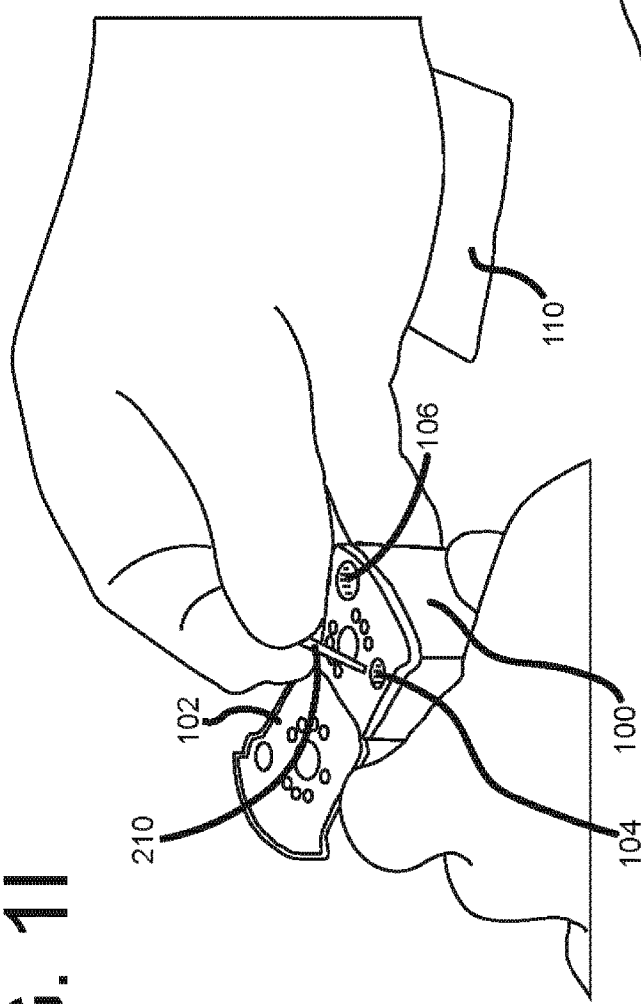
FIG. 1I is a representation of the reagent storage section of the storage device being snapped off at the break-off region.

In more detail, the customer or user inserts the narrow end of reagent storage device tip 200 into the dedicated target specific PCR component port 104 in the universal cartridge 100, as seen in FIG. 1G. As seen in FIG. 1H, the customer bends (i.e. torques or levers) the reagent storage device against the side of dedicated port 104. In response to this action, the reagent storage section 205 breaks off from the remaining section 210 of reagent storage device 200 at score line 215. Upon separation from the remaining section 210 which the user is still holding, the reagent storage section 205 with the target specific PCR component therein falls into the chamber below the dedicated target specific port 104 of universal cartridge 100. FIG. 1I depicts universal cartridge 100 and remaining section 210 after reagent storage section 205 has fallen into the chamber below dedicated port 104.

Figure 1J:
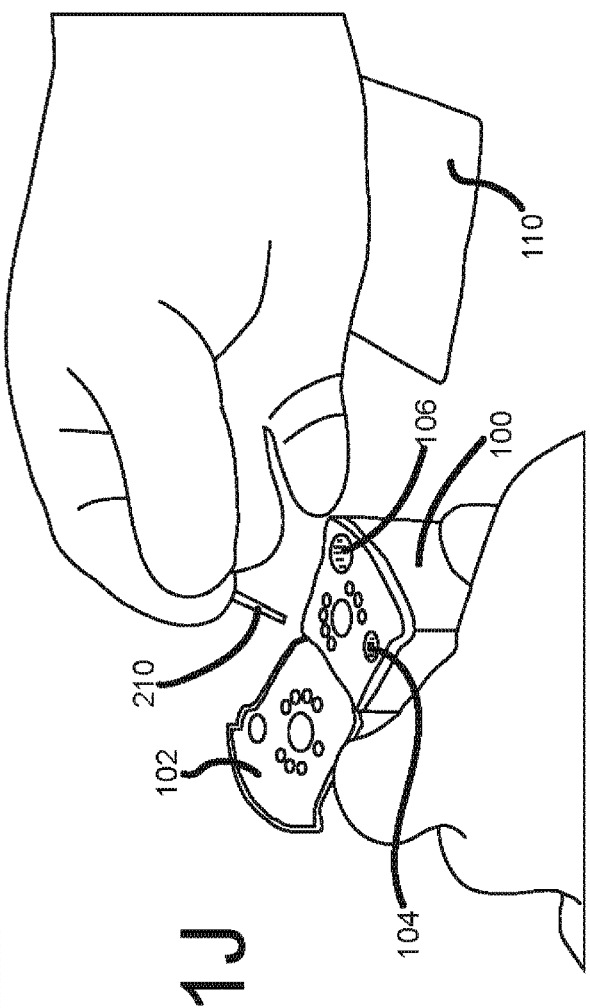
FIG. 1J is a representation of the remaining section of the storage device being moved away from the universal cartridge by the user.
Figure 1L:
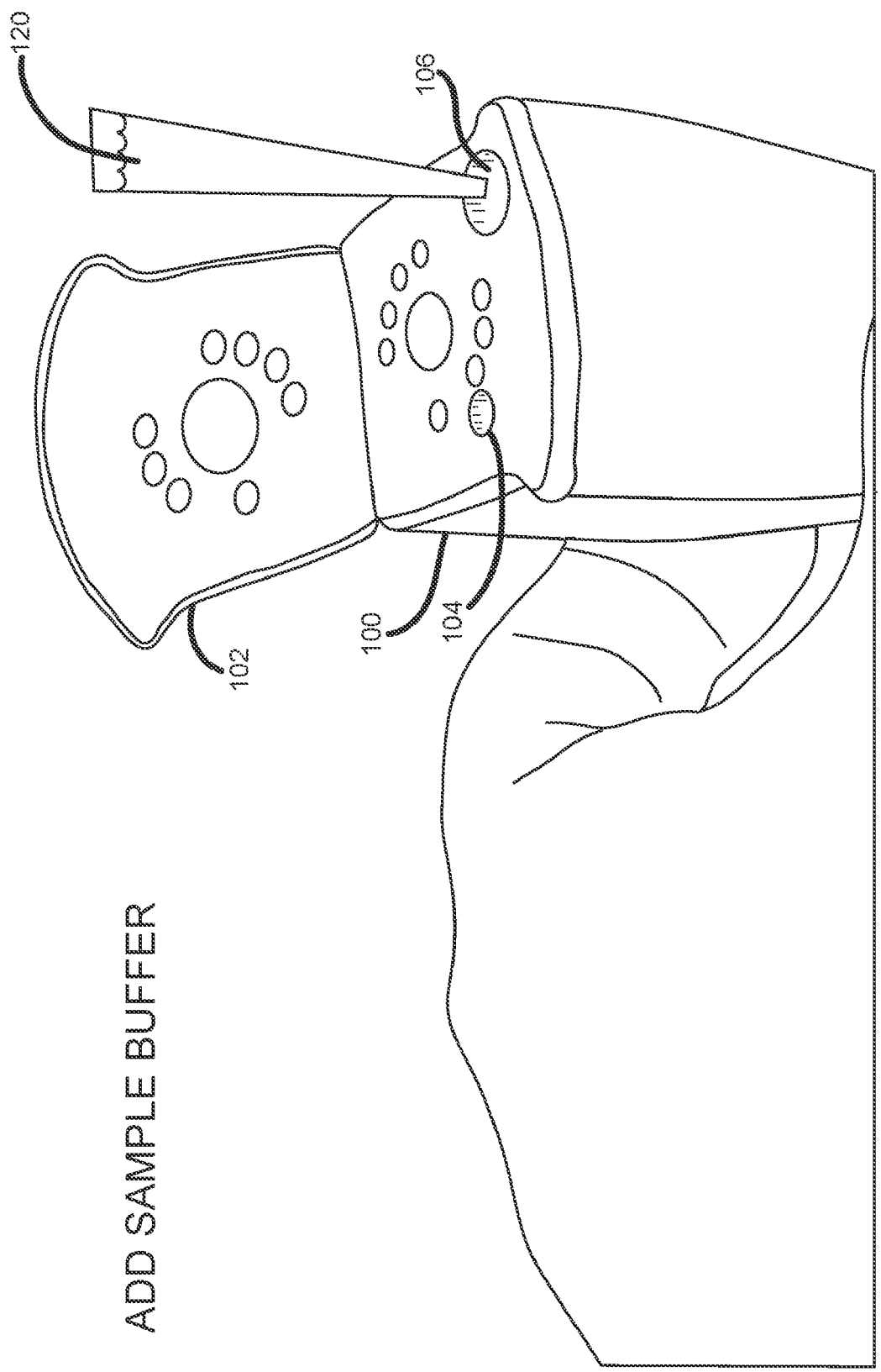
FIG. 1L depicts of a pipette being moved toward the sample port of the universal cartridge before adding the sample thereto.
Figure 1M:
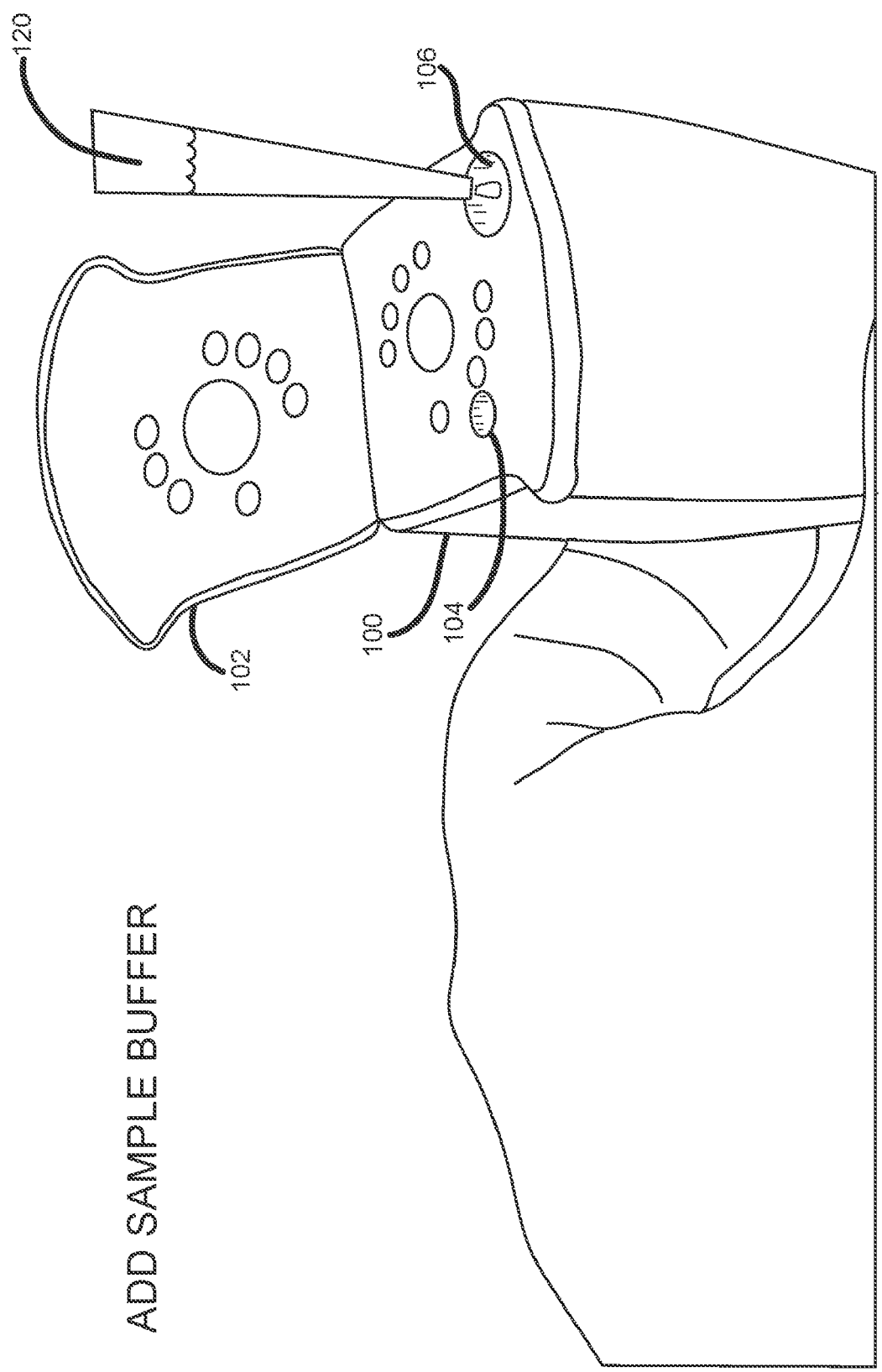
FIG. 1M depicts the pipette dispensing the sample into the sample port of the universal cartridge.

FIG. 1J depicts the user moving remaining section 210 away from universal cartridge 100 after the target specific PCR component is deposited in dedicated port 104. After adding the target specific PCR component to the target specific port 104 of the universal cartridge 100, the user or customer may add a sample buffer to sample port 106 adjacent the front right side of the cartridge, as seen in FIG. 1K. The customer adds the sample under test to the sample port 106 as seen in FIG. L and FIG. M.

Figure 1O:
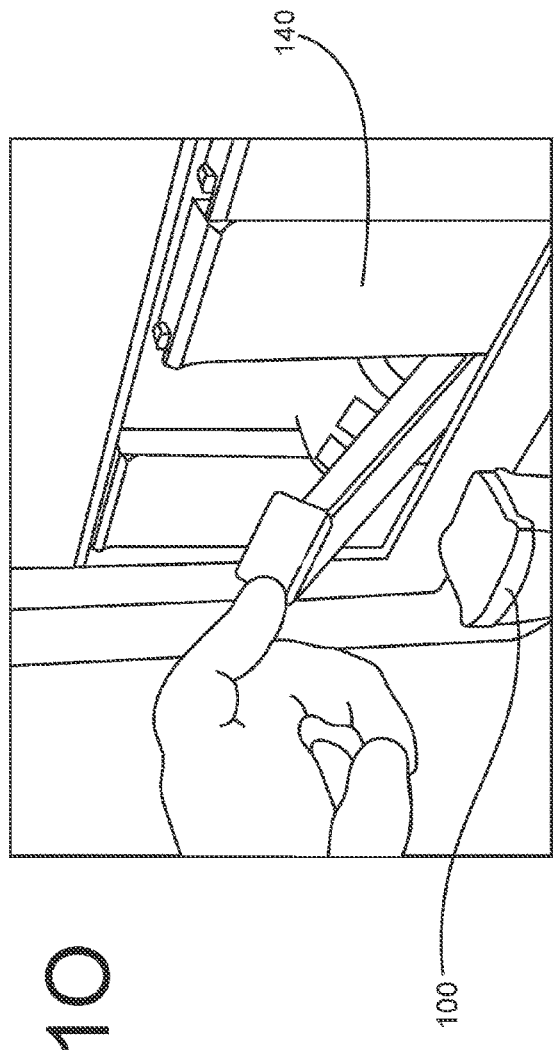
FIG. 1O depicts a user opening a bay of a test instrument in preparation for placing the universal cartridge therein.
Figure 1P:
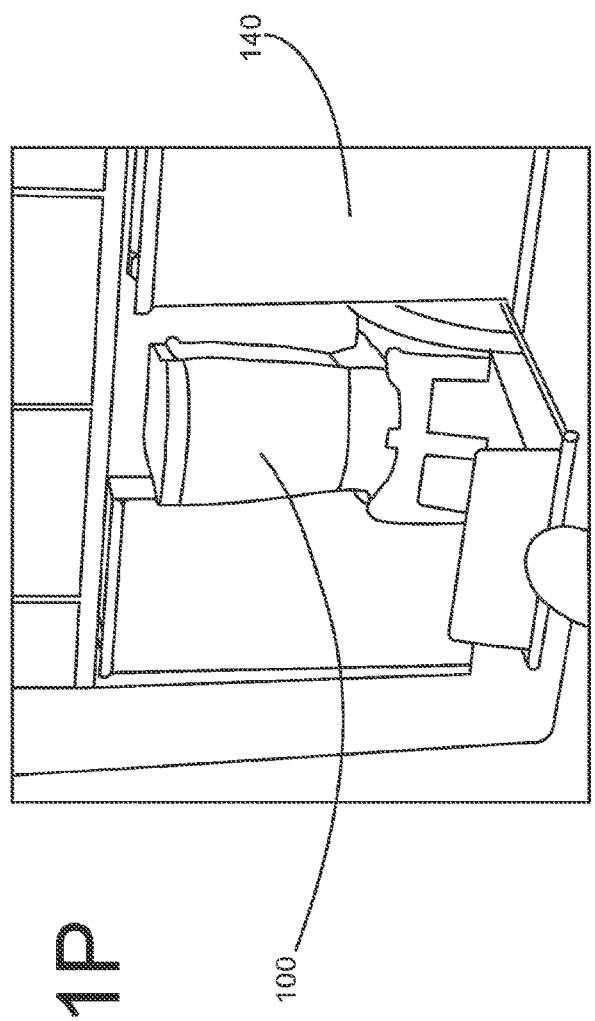
FIG. 1P depicts the universal cartridge situated in the open test bay prior to closure of the test bay and the beginning of the test.

As seen in FIG. 1N, the customer or user inputs test run information into a general-purpose computer 130 that is configured with a testing application to communicate with a molecular testing instrument 140 that is depicted in both FIG. 1O and FIG. 1P. The test run information includes information such as parameters and conditions for the particular tests to be performed by molecular testing instrument 140 using the reagents and sample now all present in the universal cartridge 100. Molecular testing instruments suitable for conducting tests with the universal cartridge 100 described herein are seen in U.S. Patent Application Publications 2014/0098252. and 2017/0021356, the disclosures of which are incorporated herein by reference in their entirety.

In more detail and as seen in FIG. 1O, the user opens the door of a bay of the testing instrument 140. The user places cartridge 100 into the bay as seen in FIG. 1P. Next, the user closes the door of the bay of the testing instrument, as seen in FIG. 1Q. Molecular testing instrument 140, working in cooperation with general purpose computer 140, provides test results on display 135 for the particular test specified in the input test run information, as seen in FIG. 1R.

Figure 2A:
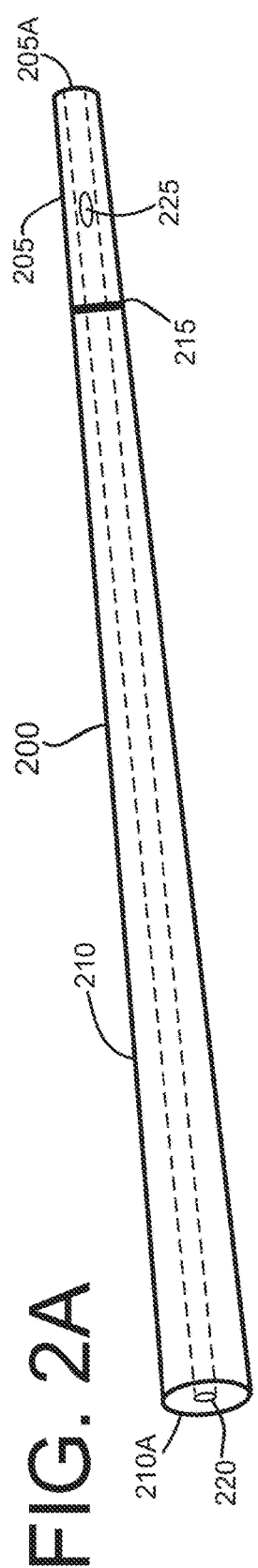
FIG. 2A is a perspective view of one embodiment of the target specific PCR component storage device.
Figure 2B:
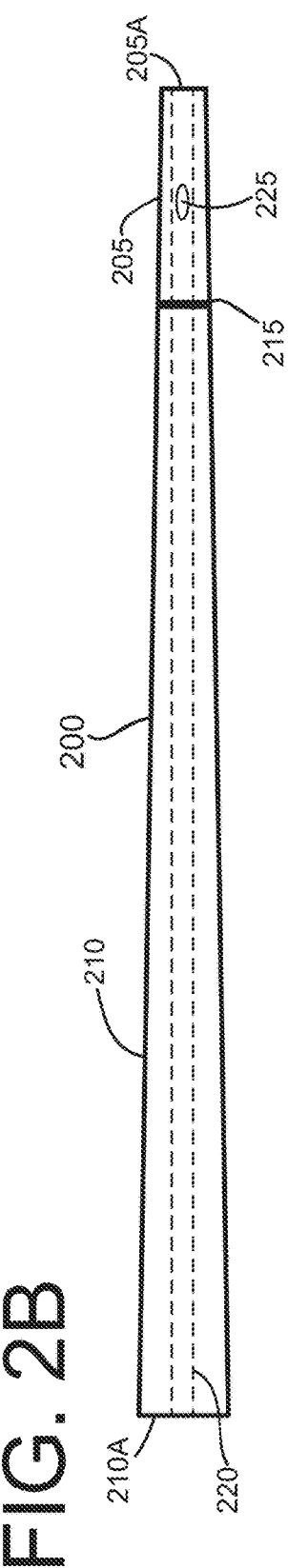
FIG. 2B is side elevational view of one embodiment of the target specific PCR component storage device.
Figure 2C:
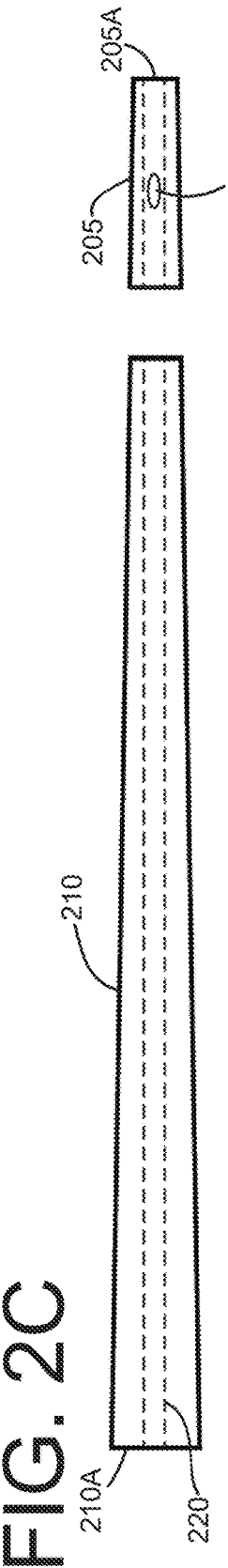
FIG. 2C depicts target specific PCR component storage device after being separated into two sections at the break-off region.

FIG. 2A is a perspective view, and FIG. 1B is a plan view, of a first embodiment of the reagent storage device 200 that employs a score line separator 215 to provide a break-off region to device 200. This break-off region may also be referred to as a snap-off region. The break-off region is intentionally structurally weakened in comparison with the remainder of device 200, so that when device 200 is bent or torqued, device 200 will break and separate at the break-off region. Score line 215 is one way to implement this break-off region so that device 200 is separable, i.e. breakable, into reagent storage section 205 and remaining section 210. FIG. 2C depicts reagent storage device 200 after it is separated at score line 215 into reagent storage section 205 and remaining section 210.

Reagent storage device 200 includes a central channel 220 (indicated in dashed lines) situated between the opposed ends of the device, namely between narrow end 205A of reagent storage section 205 and wide end 210A of the remaining section 210. The lyophilized target specific reagent 225 is positioned in the central channel 220 in reagent storage section 205, as shown. As stated above, the reagent storage device 200 may exhibit a generally conical geometry as depicted. Alternatively, the reagent storage device 200 may have a tubular or substantially cylindrical geometry, depending on the particular application. The central channel 220 may likewise exhibit a tubular or substantially cylindrical geometry as depicted, or exhibit a generally conical geometry, depending on the particular application.

Figure 3:
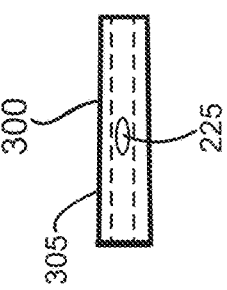
FIG. 3 depicts a standalone reagent storage device.

FIG. 3 shows a second embodiment of the reagent storage device as device 300 wherein the reagent storage section 305 is formed as a standalone unit. This embodiment may be referred to as the standalone reagent section embodiment. Reagent storage device 300 exhibits a geometry similar to reagent storage section 205 of FIG. 2C. This embodiment requires no score line. Like the first embodiment, reagent storage device 300 may be conical, tubular or cylindrical and its central channel may be conical, tubular or cylindrical.

Reagent storage devices 200, 300 and 500 may be formed as a pipette tip that is insertable into a pipette that transfers the target specific PCR component into the reagent storage device prior to lyophilization of the target specific PCR component, i.e. reagent, in the reagent storage device. In one embodiment, the reagent storage device exhibits a narrow end closest to the stored reagent 225 and a wide end farthest from the stored reagent 225. In another embodiment, both ends of the reagent storage device may exhibit the same diameter or substantially similar diameters.

Referring generally to FIG. 4A, the reagent storage device may employ a 405 cap placed over one of the ends of the tube of the reagent storage device, such as device 300, of FIG. 3 to enable the user to pick up the reagent storage device 300 with a gloved hand via the cap 405 while avoiding contamination of the reagent storage device 300 by the user. In one embodiment, wherein the reagent storage device exhibits a narrow end and a wide end, the cap 405 is placed over the narrow end. Alternatively, the cap 405 is placed over the wide end. If the reagent storage device exhibits same size ends, i.e. same diameter opposed ends, the cap is placed over either opposed end to facilitate transfer of the reagent storage device to the dedicated target specific port in the universal cartridge 100 while avoiding contamination.

Cap 405 of FIG. 4A includes at least one open end that is placed over one of the ends of the reagent storage device 300. In the embodiment depicted, cap 405 is a sleeve of flexible plastic material that includes two open in FIG. 4A. Either end of this dual open-ended cap may be placed over an end of reagent storage device 300. The user slightly squeezes the flexible cap 405 sufficiently to hold an end of the reagent storage device 300 therein. The user, now grasping the reagent storage device 300 via the cap 405, moves the reagent storage device 300 over the dedicated port 104 in universal cartridge 100. The user reduces the squeezing action on cap 405 to allow the reagent storage device 300 to fall into the chamber below the dedicated port 104. Subsequently, the lyophilized target specific PCR component may be rehydrated and testing is conducted in the testing instrument. Alternatively, rehydration may be performed at an earlier time.

In another embodiment shown in FIG. 4B and FIG. 4C, an improved cap 415 includes a flexible bulbous ejector 420 that facilitates the user in ejecting the reagent storage device 300 from cap 415 when the user desires to place the reagent storage device 300 in the dedicated port 104 of universal cartridge 100. In this embodiment, improved cap 415 is still sleeve-like in that it fits over an end of the reagent storage device 300, but one end of cap 415 is closed. For example, as seen in FIGS. 4B and 4C, the closed end of the cap 415 may include a flexible bulbous ejector 420 that the user squeezes to push the end of the reagent storage device out of cap 415 and into the dedicated port 104 of cartridge 100. FIG. 4C shows cap 415 installed on one end of the reagent storage device 300. Cap 415 may be installed on an open end of the sleeve-shaped cylindrical reagent storage device 300 described above or an open end of a conically-shaped reagent storage device. In actual practice, if a conically-shaped reagent storage device is employed, cap 415 is installed on the narrow end of the reagent storage device. Alternatively, cap 415 may be installed on the wide end of the reagent storage device. Alternatively, instead of the cap described above, the reagent storage device 300 may include a small handle that the user may grasp while moving the reagent storage device 300 to the dedicated port 104 of the universal cartridge 100.

Figure 5A:
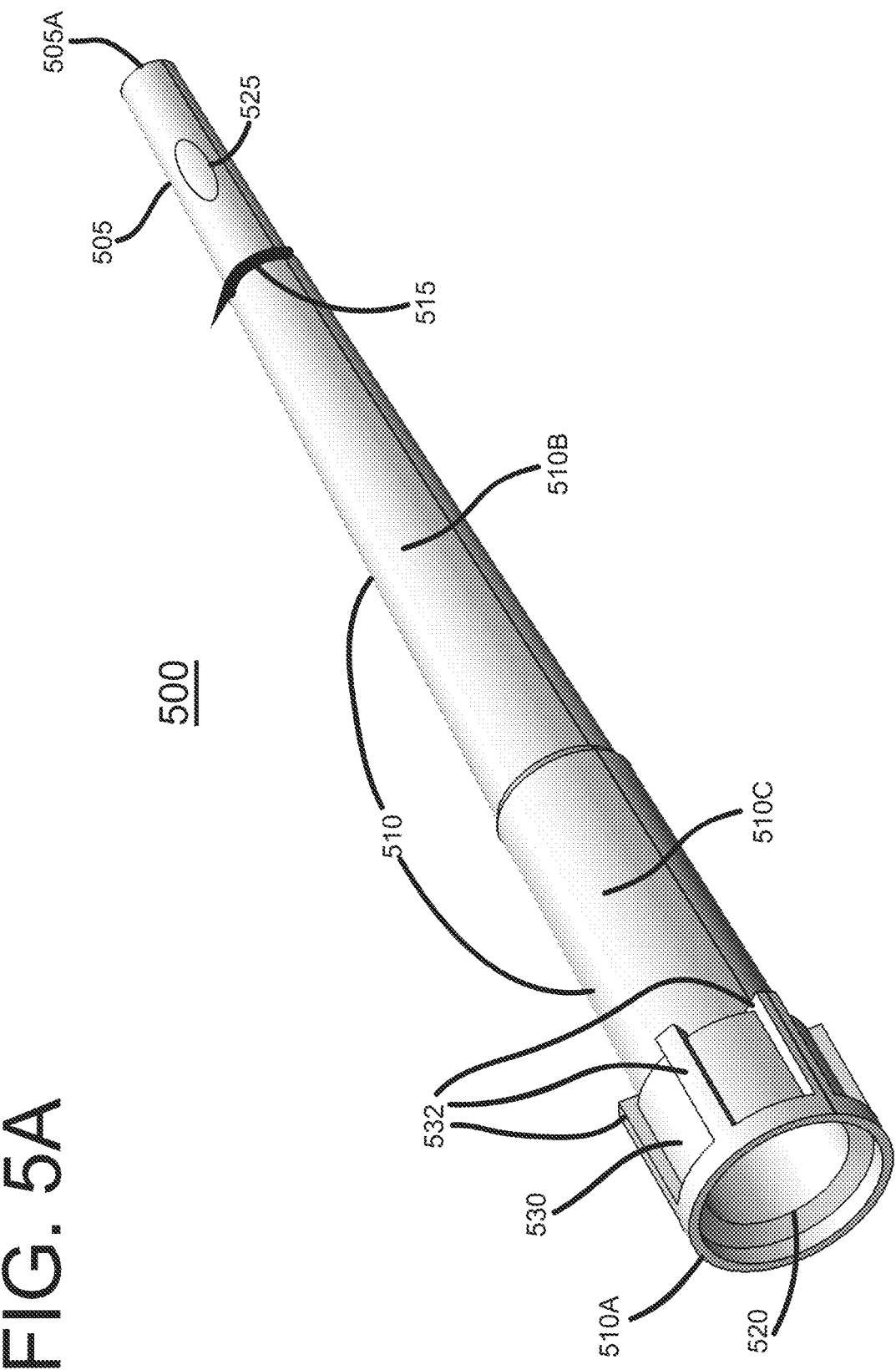
FIG. 5A is a perspective view of another embodiment of the target specific PCR component storage device.

FIG. 5A shows a perspective view of the preferred embodiment of the reagent storage device as device 500. Reagent storage device 500 may also be referred to as a "tip". Device 500 includes a break-off region 515 at which device 500 intentionally breaks when device 500 is inserted into dedicated port 104 of universal cartridge 100 and is bent or torqued in the manner described above. Breaking, i.e. snapping off, device 500 at break-off region 515 separates device 100 into 2 structures, namely reagent storage section 505 and remaining section 510. Reagent storage device 500 is fabricated of a moldable plastic material such as high purity polypropylene, medical grade polystyrene, or polydimethylsiloxane (PDMS) silicones, for example. Reagent storage device 500 is fabricated to be transparent, translucent or opaque, as desired. In any case, target specific PCR component 525 is drawn to be visible in FIG. 5A although it is situated in central channel 520 which is interior to device 500.

In this embodiment, the geometry of device 500 is generally conical from wide end 510A to narrow end 505A. In other words, reagent storage section 505 is generally conical and exhibits an increasing diameter as distance increases from narrow end 505A. In this particular embodiment, remaining section 510 includes subsections 510B and 510C, each of which are generally conical as shown. More particularly, middle subsection 510B is conical and exhibits generally increasing diameter from break-off region 515 to wide-end subsection 510C. Device 500 includes a collar 530 at wide end 510A as shown. Collar 530 includes castellation elements 532 that increase the rigidity of collar 530 and wide end 510A to facilitate the reliable mounting of wide end 510A to a mandrel or shaft of a liquid handling system or alternatively to a micropipette. When reagent storage device 500 is so mounted, the target specific PCR component 525 can be drawn up into narrow end 505A before freezing and lyophilization. Reagent storage device 500 may also be so mounted to dispense water into wide end 510A to rehydrate target specific PCR component 525 before dispensing the rehydrated target specific PCR component 525 into dedicated port 104 of universal cartridge 100.

As seen in FIGS. 5B and 5C, device 500 is molded in two pieces, namely top portion 500A and bottom portion 500B as evidenced by mold lines 542 and 544. After molding, top portion 500A and bottom portion 500B may be fused together using heat and pressure.

Break-off region 515 is formed in top portion 500A and bottom portion 500B during the molding process. At break-off region 515, reagent storage device 500 is intentionally structurally weakened in comparison with the structural integrity of the remainder of the device. In this manner, when reagent storage section 505 is inserted in dedicated port 104 and bent against the interior of port 104, reagent storage section 505 breaks away from remaining section 510. Consequently, reagent storage section 505 with the user selected target specific PCR component 525 therein falls into dedicated port 104. This completes the "programming" of universal cartridge 100 for use in a test that targets a sequence corresponding to the particular target specific PCR component 525.

FIG. 5D shows a cross-section of reagent storage device 500 taken along section line 5D-5D of FIG. 5B. More particularly, FIG. 5D shows a break-off region that is implemented as a V-shaped groove 517 in the exterior surface of device 500. FIG. 5D' shows a break-off region that is implemented as a V-shaped groove 517 in the exterior surface of device 500 and a coaxial V-shaped groove in the interior surface of device 500, i.e. a coaxial V-shaped groove in central channel 520. In alternative embodiments, grooves 517 and 519 may exhibit other geometries, such as U-shaped for example, as long as the selected geometry provides break-off region 515 with sufficient structural weakness that it breaks when bent or torqued in dedicated port 104 as described above. Selecting a geometry that generally narrows the thickness of the tubular member that forms device 500 at break-off region 515 can provide the desired break-off or snap-off feature to device 500.

FIG. 5E is an end view of reagent storage device 500 as viewed from narrow end 505A. FIG. 5E shows mainly the exterior of device 500. FIG. 5F is an end view of reagent storage device 500 as viewed from wide end 510A. FIG. 5F shows mainly the interior of device 500.

Figure 6A:
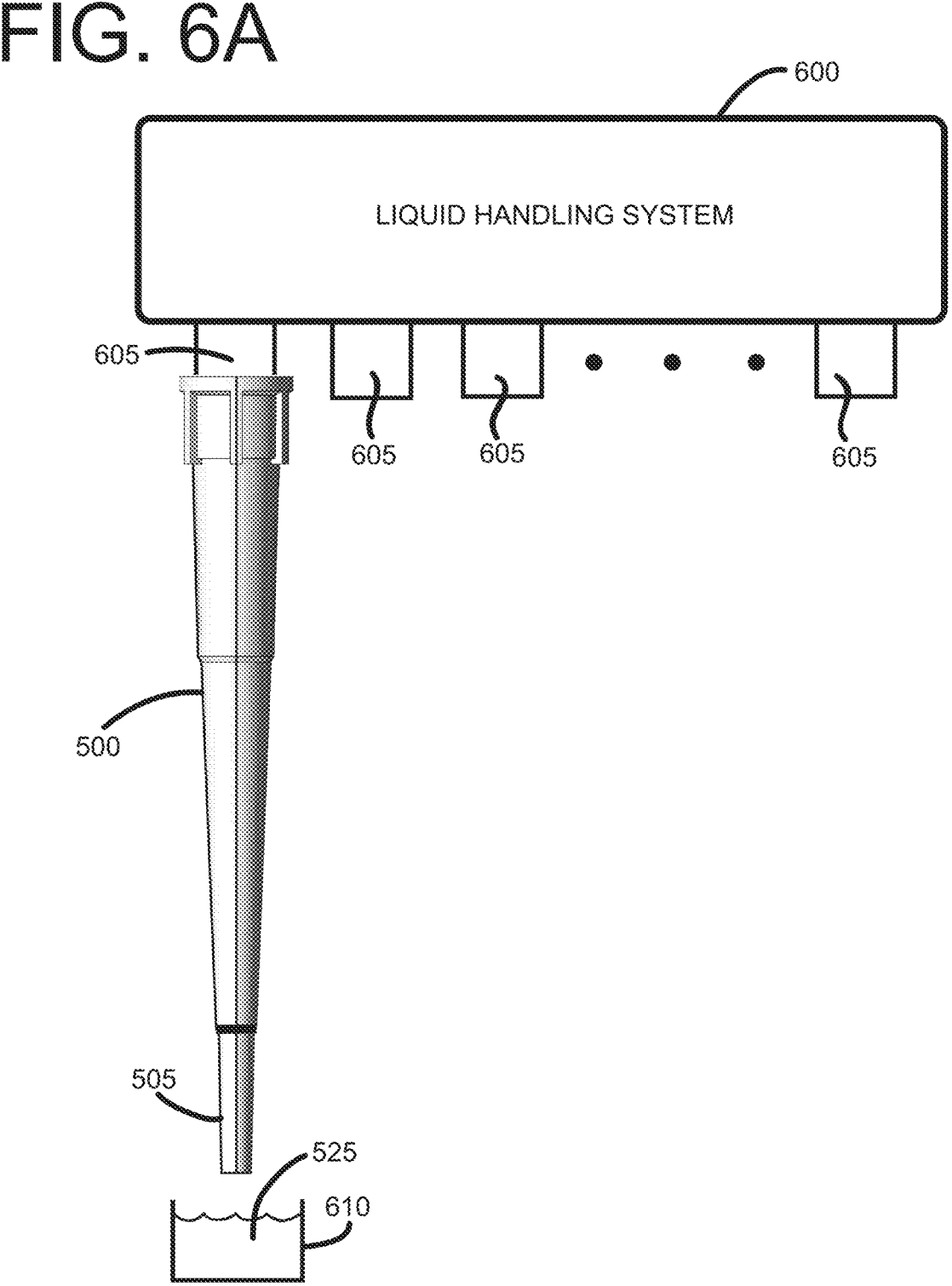
FIG. 6A is representation of the target specific PCR component storage device installed on a shaft or mandrel of a liquid handling system prior to drawing the target specific PCR component liquid reagent into the storage device.

FIG. 6A shows a simplified liquid handling system (LHS) 600 that includes multiple shafts 605 or mandrels on which reagent storage device 500 may be mounted to draw a reagent, namely the target specific PCR component, into device 500 for storage. When so mounted, LHS 600 may alternatively dispense liquid into reagent storage device 500 to rehydrate a lyophilized target specific PCR component stored within device 500 prior to dispensing into the dedicated port 104 of universal cartridge 100, as described above. Reagent storage device 500 may alternately be coupled to a micropipette (not shown) for these same purposes.

Figure 6B:
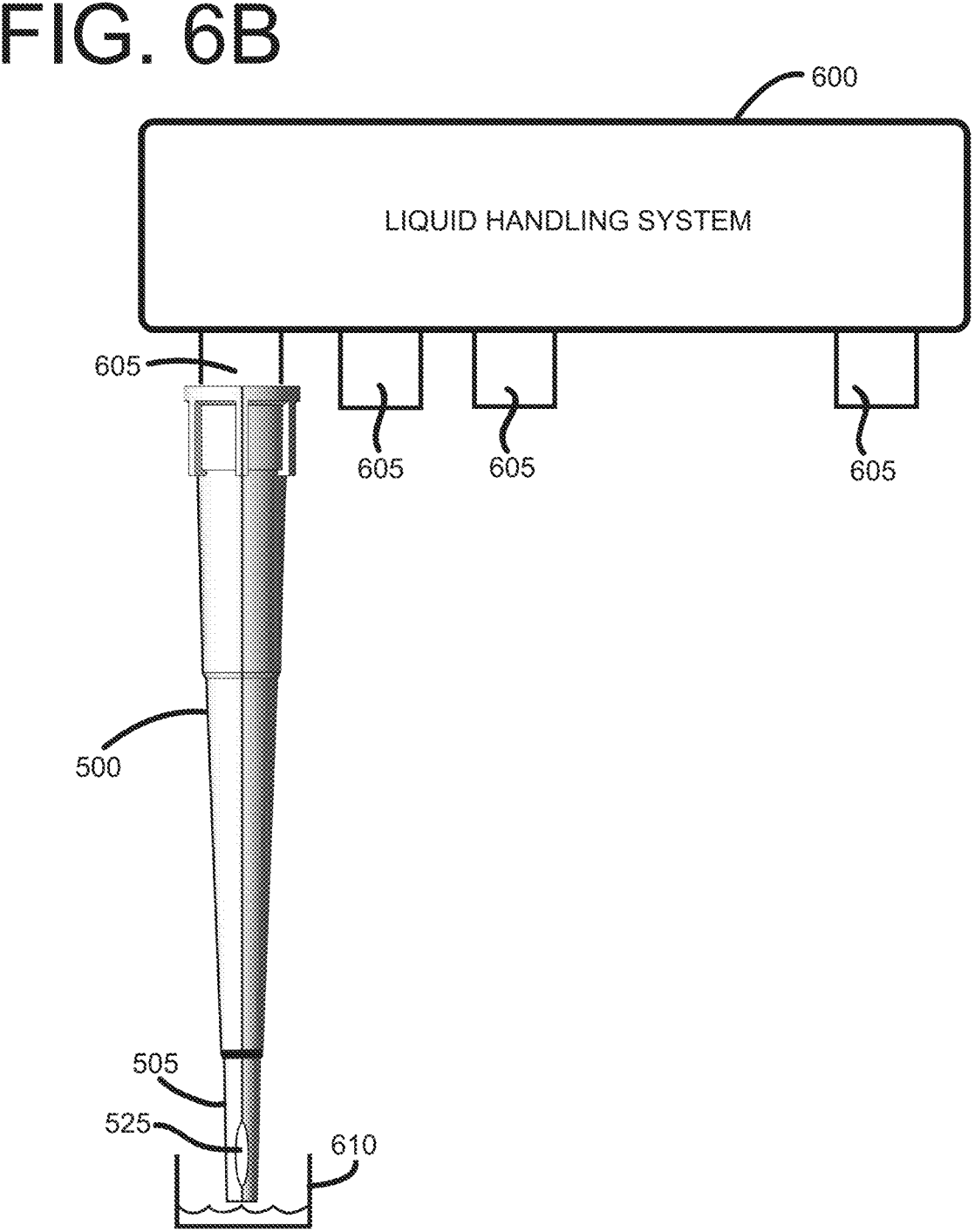
FIG. 6B is representation of the target specific PCR component storage device installed on a shaft or mandrel of a liquid handling system after drawing the target specific PCR component liquid reagent into the storage device.

Specifically, FIG. 6A shows LHS 600 configured with reagent storage device 500 situated on a shaft 605 or mandrel such that LHS 600 can draw the target specific PCR component reagent 525 (in liquid form) from reservoir 610 into reagent storage section 505. FIG. 6B shows LHS 600 after successfully drawing reagent 525 into reagent storage section 505. Reagent 525 within reagent storage section 505 of may now be frozen and lyophilized by using appropriate refrigeration and lyophilization apparatus.

Figure 7A:
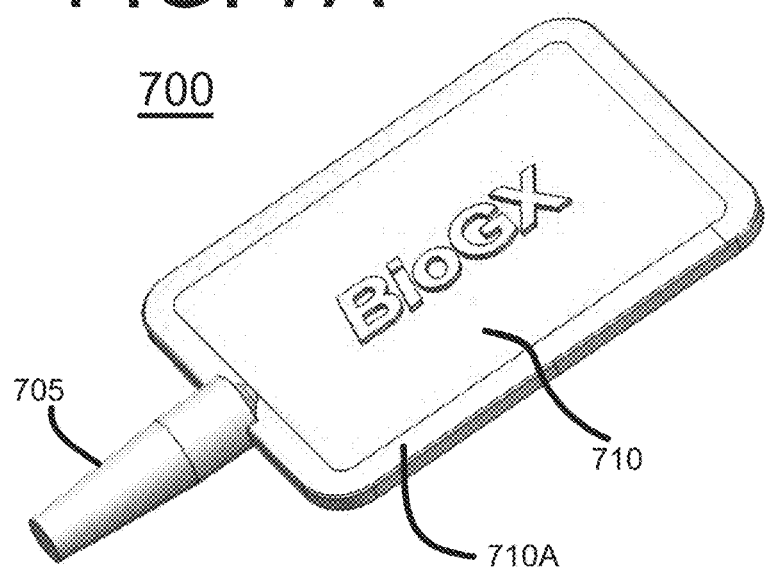
FIG. 7A is a perspective view the disclosed dual purpose tab that includes both a plug and a planar portion with a barcode ID label thereon.

FIG. 7A shows a dual-purpose tab 700 that includes a plug portion 705 that is dimensioned to fit into and plug, i.e. seal, wide end 510A of target specific reagent storage device 500. As depicted, plug portion 705 is generally conical. In one embodiment, dual-purpose tab 700 also includes a planar tab portion 710 with opposed sides 710A and 710B.

Figure 7B:
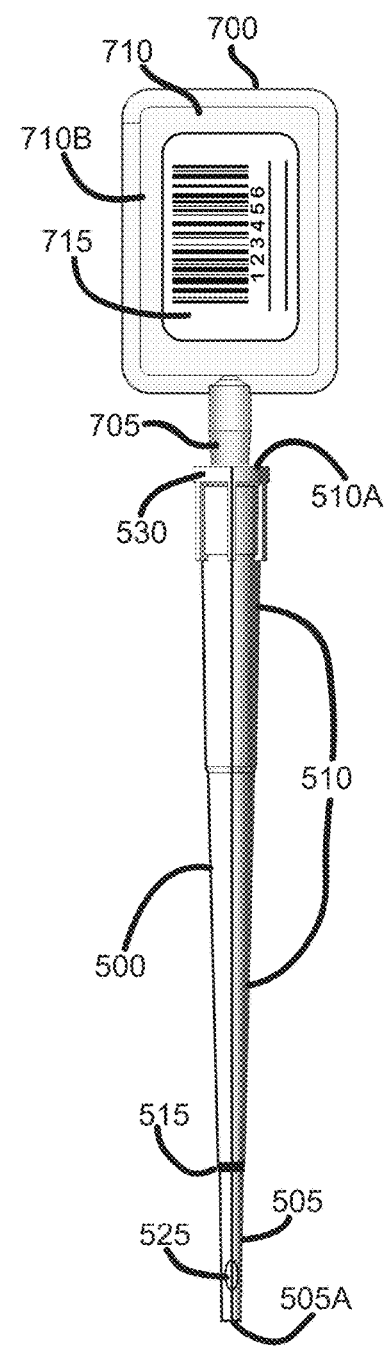
FIG. 7B depicts the tab of FIG. 7A being plugged into the wide end of the target specific PCR component storage device.

FIG. 7B shows dual purpose tab 700 with plug portion 705 situated in the central channel of reagent storage device 500 at the wide end 510A thereof. Side 710B of tab 700 includes a removably attached identification label 715, for example a barcode label, that uniquely identifies the particular target specific PCR component 525 in reagent storage device 500. Identification label 715 may be adhesively attached to side 710B of tab portion 710. Identification label 715 is placed on tab portion 710 after LHS 600 draws the target specific PCR component 525 into reagent storage device 500 and target specific PCR component 525 is frozen and lyophilized, as per the discussion of LHS 600 with reference to FIGS. 6A and 6B above. Tab 700 thus provides both a unique identifier and a convenient way for the user to hold the target specific PCR component reagent storage device 500.

Figure 7C:
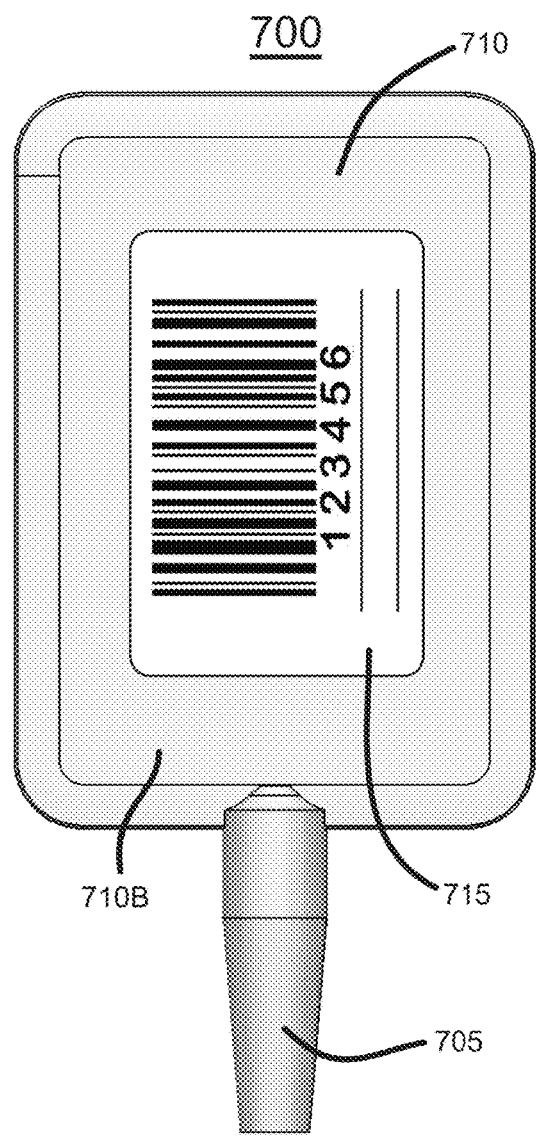
FIG. 7C depicts one side of the tab of FIG. 7A with the barcode ID thereon.
Figure 7D:
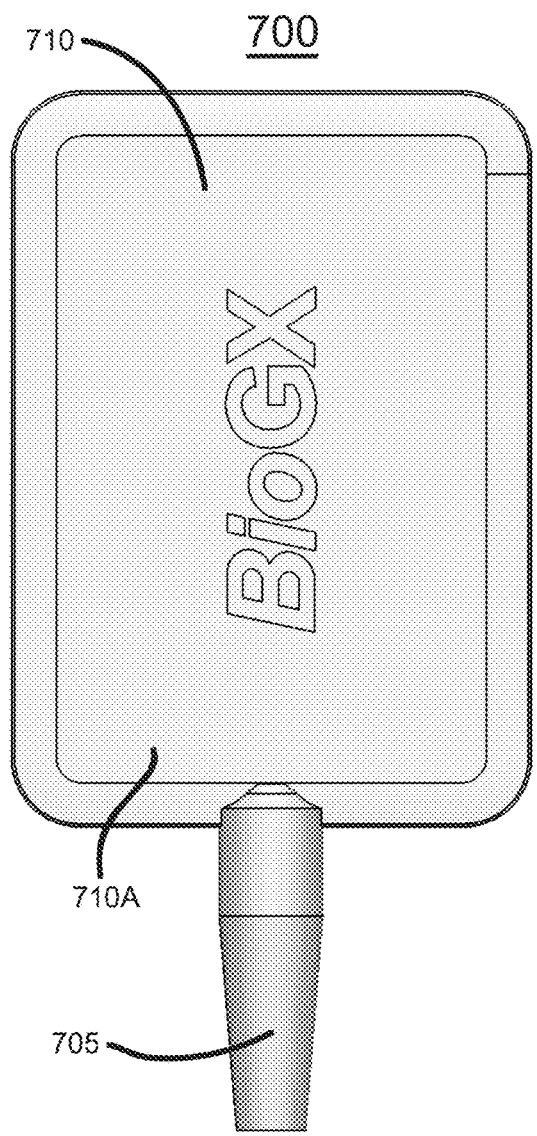
FIG. 7D depicts the side of the tab opposite the barcode ID side depicted in FIG. 7C.
Figure 7G:
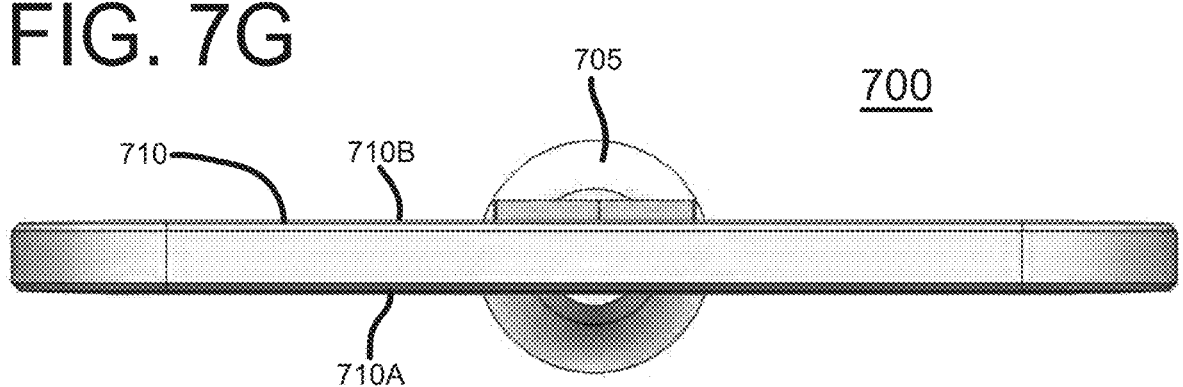
FIG. 7G is first end view of the tab of FIG. 7A.
Figure 7H:
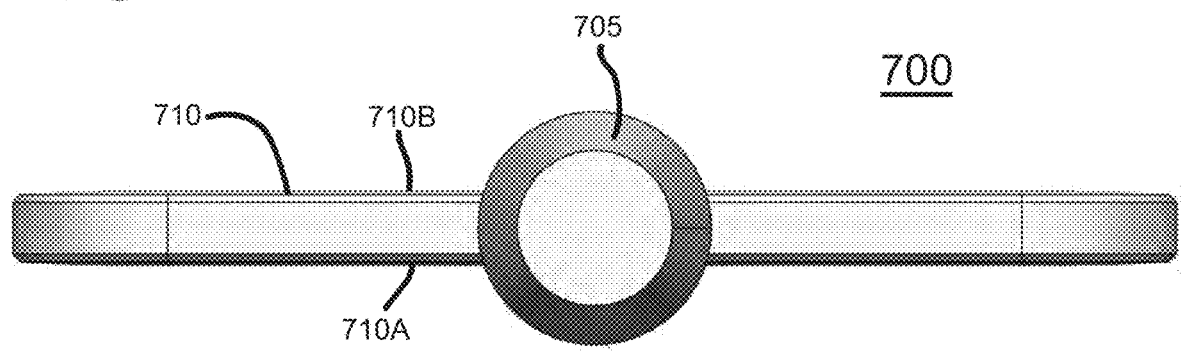
FIG. 7H is second end view of the tab of FIG. 7A.

FIG. 7C and FIG. 7D respectively provide front and back views of tab 700. FIG. 7E and FIG. 7F respectively provide right side and left side elevational views of tab 700. FIG. 7G and FIG. 7H respectively provide first and second end views of tab 700.

The customer or user may use tab 700 in two different ways when tab 700 is installed in the wide end 510A of reagent storage device 500, as depicted in FIG. 7B. In a first use, the user can remove tab 700 from reagent storage device 500 (with the lyophilized target specific PCR component reagent therein) and reinsert device 500 on shaft 605 of the liquid handling system 600 of FIG. 6A. LHS 600, via its shaft 605, may draw water or buffer up from a reservoir in fluidic communication with reagent storage section 505 at narrow end 505A. The drawn fluid rehydrates the lyophilized target specific PCR component 525. The rehydrated target specific PCR component 525 in reagent storage device 500 may now be dispensed into dedicated port 104 of universal cartridge 100. This dispensing action may be performed using the break-off region method described above in detail. As an alternative to employing LHS 600 for rehydration, the user may install device 500 in a micropipette to perform rehydration prior to dispensing the rehydrated target specific PCR component 525 into dedicated port 104 of universal cartridge 100 using the above-described break-off region method.

In a second use of tab 700, the user may opt to leave tab 700 installed in wide end 510A of reagent storage device 500. In this user scenario, the user inserts the reagent storage section 505 into dedicated port 104 of universal cartridge 100 and uses the break-off region dispensing method described above. Reagent storage section 505 thus snaps or breaks off, and the target specific PCR component reagent 525 in reagent storage section 505 is deposited in port 104 of universal cartridge 100. After completing this dispensing action, the user removes the barcode ID label 715 from tab 700 and affixes barcode label 715 to the top of universal cartridge 100. In this manner, now that the target specific PCR component reagent 525 is inside universal cartridge 100, the relocated barcode label 715 now on cartridge 100 identifies this particular cartridge as containing the reagent that just dropped into cartridge 100.

The varied embodiments described above may exhibit different respective desirable features. In one embodiment, the disclosed reagent storage device enables the rapid menu expansion of testing options for users. As discussed above, universal cartridge 100 stores generic reagents applicable to a number of different tests, but does not initially store a target specific PCR component reagent that targets a particular sequence desired by the user for a particular test. The user is empowered to effectively customize a test to target a particular sequence. This is achieved uniquely by dispensing the target specific PCR component stored in the disclosed reagent storage device which includes the special break-off region as described above. Users may now conduct different types of tests with different specimens and targeting different sequences without the need for a massive and expensive inventory of cartridges that contain all reagents for all possible desired tests.

The universal cartridge stores generic reagents for testing, but also includes a dedicated port that receives a target specific PCR component that customizes the test to be performed using the universal cartridge. In one embodiment, after dispensing the target specific PCR component into the dedicated port using the above-described break off region method, when the user moves the unique barcode label from the tab to the universal cartridge, this signifies that the universal cartridge is effectively programmed to perform a dedicated test.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    (a) providing a universal reagent cartridge including a plurality of chambers that are preloaded with predetermined non-target-specific reagents therein, the universal reagent cartridge including a sample port and a dedicated target-specific reagent port, the universal reagent cartridge not including a target-specific reagent prior to the following inserting step (c);
    (b) providing a custom target-specific reagent storage device that stores a lyophilized, target-specific reagent therein, wherein the custom target-specific reagent storage device includes a first portion containing the target-specific reagent and a second portion that is separable from the first portion, wherein the first portion is end user insertable into the dedicated target-specific reagent port of the universal reagent cartridge to customize the universal reagent cartridge with the target-specific reagent;
    (c) inserting the first portion of the custom target-specific reagent storage device containing the target-specific reagent into the dedicated port of the universal reagent cartridge;
    (d) separating the first portion of the custom target-specific reagent storage device containing the target-specific reagent from the second portion of the custom target-specific reagent storage device while the first portion of the custom target-specific reagent storage device is in the dedicated port of the universal reagent cartridge, such that the first portion of the custom target-specific reagent storage device with the target-specific reagent therein falls into the universal cartridge; and
    (e) removing the second portion of the custom target-specific reagent storage device from the dedicated port of the custom target-specific reagent storage device after the first portion of the custom target-specific reagent storage device with the target-specific reagent therein falls into the universal cartridge.

2. The method of claim 1, wherein the target-specific reagent is a lyophilized, target-specific polymerase chain reaction (PCR) component.

3. The method of claim 2, wherein the target-specific reagent is designated for a predetermined target DNA or RNA gene sequence in a sample.

4. The method of claim 3, further comprising adding a sample buffer to the sample port of the universal reagent cartridge.

5. The method of claim 3, further comprising adding a sample under test to the sample port of the universal reagent cartridge.

6. The method of claim 1, wherein the first portion of the custom target-specific reagent storage device with the target-specific reagent therein is separable from the second portion of the custom target-specific reagent storage device via a score line between the first portion of the custom target-specific reagent storage device with the target-specific reagent therein and the second portion of the custom target-specific reagent storage device at which the first portion of the custom target-specific reagent storage device with the target-specific reagent therein snaps off from the second portion of the custom target-specific reagent storage device.

7. The method of claim 1, wherein the first portion of the custom target-specific reagent storage device with the target-specific reagent therein is separable from the second portion of the custom target-specific reagent storage device via a break-off region between the first portion of the custom target-specific reagent storage device and the second portion of the custom target-specific reagent storage device.

8. The method of claim 7, further comprising breaking off the first portion of the custom target-specific reagent storage device with the target-specific reagent therein from the second portion of the custom target-specific reagent storage device at the break-off region after inserting the first portion of the custom target-specific reagent storage device with the target-specific reagent therein into the dedicated port of the universal reagent cartridge.

\* \* \* \* \*